United States Patent [19]
Wildman

[11] Patent Number: 5,474,444
[45] Date of Patent: Dec. 12, 1995

[54] MULTIWIRE ARCH SYSTEM

[76] Inventor: Alexander J. Wildman, 2440 Willamette St., Eugene, Oreg. 97405

[21] Appl. No.: 121,180

[22] Filed: Sep. 14, 1993

Related U.S. Application Data

[63] Continuation-in-part of Ser. No. 842,234, Feb. 26, 1992, Pat. No. 5,295,886, which is a continuation-in-part of Ser. No. 684,053, Apr. 11, 1991, Pat. No. 5,100,316, which is a continuation-in-part of Ser. No. 472,362, Jan. 29, 1990, Pat. No. 5,011,406, which is a continuation-in-part of Ser. No. 249,453, Sep. 26, 1988, Pat. No. 4,909,735.

[51] Int. Cl.$^6$ .................................................. A61C 7/00
[52] U.S. Cl. ................................................. 433/8; 433/18
[58] Field of Search ........................... 433/8, 9, 10, 13, 433/16, 18, 22, 15

[56] References Cited

U.S. PATENT DOCUMENTS

| | | |
|---|---|---|
| 678,453 | 7/1901 | Angle . |
| 1,552,413 | 8/1925 | Angle . |
| 1,584,501 | 5/1926 | Angle . |
| 1,821,171 | 9/1931 | Atkinson . |
| 1,949,444 | 3/1934 | Angle . |
| 1,952,320 | 3/1934 | Johnson . |
| 2,023,849 | 12/1935 | McCoy . |
| 2,196,516 | 4/1940 | Atkinson . |
| 2,305,916 | 12/1942 | Atkinson . |
| 2,406,527 | 8/1946 | Berke . |
| 2,665,480 | 1/1954 | Johnson . |
| 2,705,367 | 4/1955 | Berke . |
| 2,756,502 | 7/1956 | Bowles . |
| 2,759,265 | 8/1956 | Johnson . |
| 2,854,747 | 10/1958 | Lewis . |
| 3,128,553 | 4/1964 | Begg . |

(List continued on next page.)

OTHER PUBLICATIONS

Ormco® Corporation, 1332 South Lone Hill Avenue, Glendora, California 91740, 1993 catalog, p. 27.

Wildman, Alexander J., "The Future of Lingual Orthodontics," Orthodontics: Evaluation and Future, Proceedings of the International Conference of the Orthodontic Dept. of Univ. of Nymegen, The Netherlands, Oct. 22–24, 1987, pp. 261–280 (1988).

Primary Examiner—Cary E. O'Connor
Attorney, Agent, or Firm—Marger, Johnson, McCollom & Stolowitz

[57] ABSTRACT

A multiarch assembly comprises first and second parallel archwires, each formed into a segment of an orthodontic archform spanning a plurality of a patient's teeth, a multiarch bracket having a bracket body defining reentrant archwire slots along opposite occluso-gingival sides of the base for receiving and seating the first and second archwires in a base portion therein, the base portions of the slots having a predetermined center-to-center occluso-gingival spacing; and an interarch connector having a connector body formed of a resilient material with first and second archwire openings spaced apart along an occluso-gingival axis of elongation and sized for the first and second archwires to be threaded therethrough, the connector body being resiliently deformable along the axis of elongation to enable the archwires to be spread apart and then to urge the archwires toward one another in a direction of contraction along the axis of elongation;

the holes in the interarch connector being spaced center-to-center a distance approximately equal to or less than the center-to-center spacing between the base portions of the occluso-gingival spacing of the archwire slots on opposite sides of the bracket;

whereby the archwires, multiarch bracket and interarch connector exert force on the bracket, and thereby on the patient's teeth, with gradually increasing precision as the occluso-gingivally spaced archwires are urged by contraction of the interarch connector toward one another into the base portions of the spaced slots.

33 Claims, 13 Drawing Sheets

U.S. PATENT DOCUMENTS

| | | | |
|---|---|---|---|
| 3,193,930 | 7/1965 | Bien | 433/18 |
| 3,302,288 | 2/1967 | Tepper. | |
| 3,477,128 | 11/1969 | Andrews. | |
| 3,593,421 | 7/1971 | Brader. | |
| 3,660,900 | 5/1972 | Andrews. | |
| 3,748,740 | 7/1973 | Wildman. | |
| 3,775,850 | 12/1973 | Northcutt. | |
| 3,780,437 | 12/1973 | Wildman. | |
| 3,842,503 | 10/1974 | Wildman. | |
| 3,854,207 | 12/1974 | Wildman. | |
| 4,077,126 | 3/1978 | Pletcher. | |
| 4,337,037 | 6/1982 | Kurz | 433/8 |
| 4,386,908 | 6/1983 | Kurz | 433/9 |
| 4,443,189 | 4/1984 | Wildman | 433/10 |
| 4,492,573 | 1/1985 | Hanson | 433/11 |
| 4,494,931 | 1/1985 | Wildman | 433/8 |
| 4,551,094 | 11/1985 | Kesling | 433/8 |
| 4,712,999 | 12/1987 | Rosenberg | 433/8 |
| 4,713,001 | 12/1987 | Klein et al. | 433/18 |
| 4,909,735 | 3/1990 | Wildman | 433/24 |
| 5,011,406 | 4/1991 | Wildman | 433/24 |
| 5,035,614 | 7/1991 | Greenfield | 433/18 |
| 5,100,316 | 3/1992 | Wildman | 433/24 |

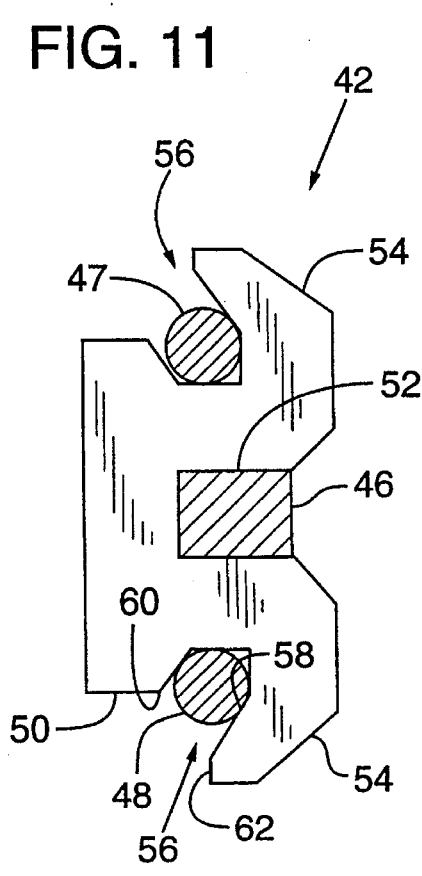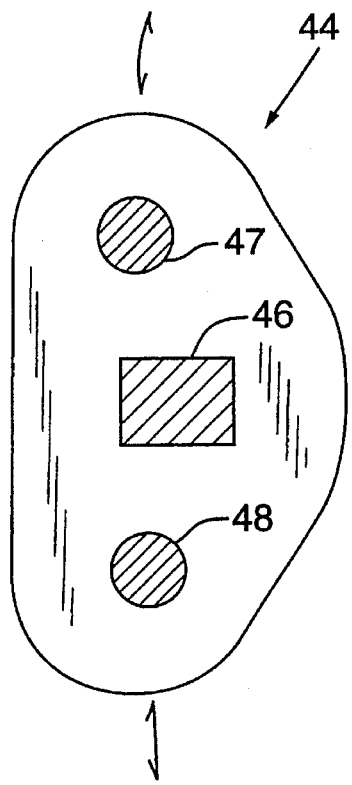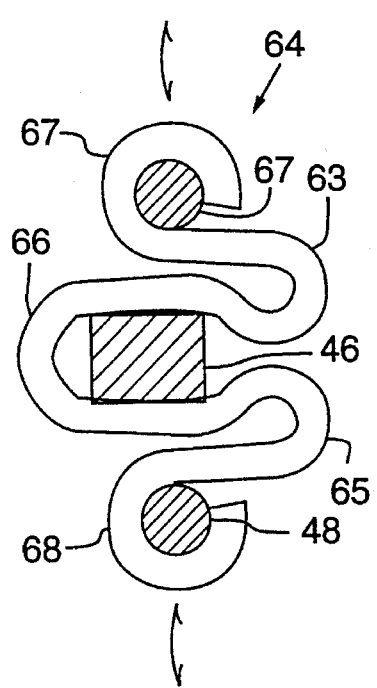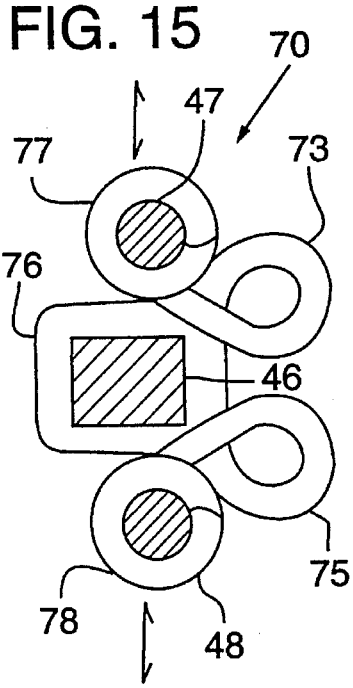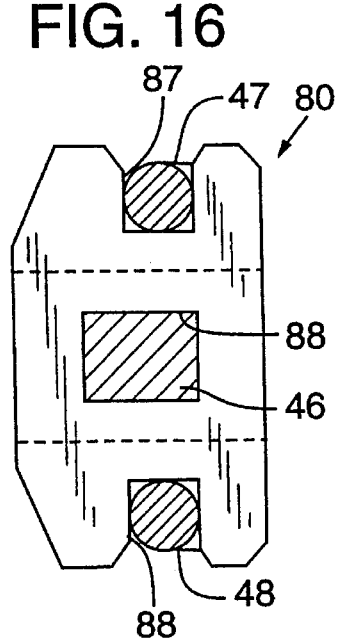

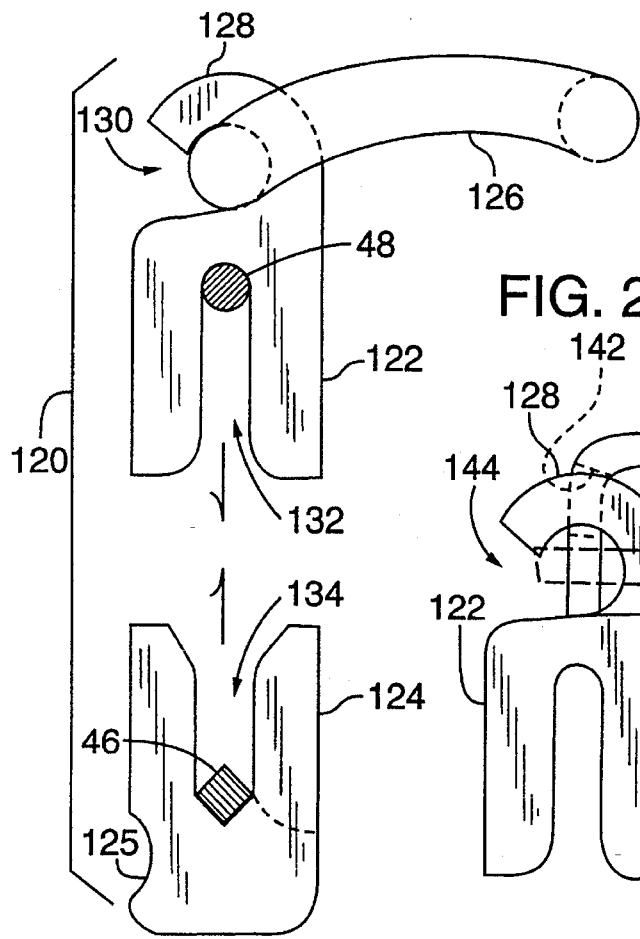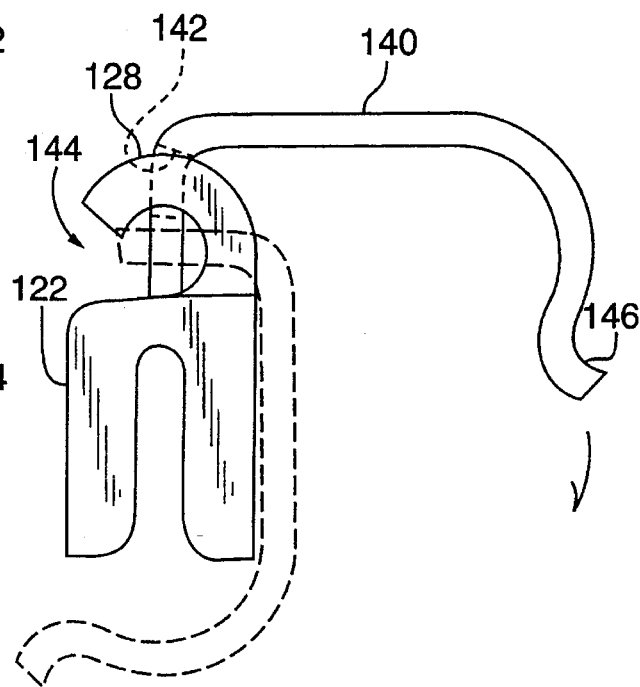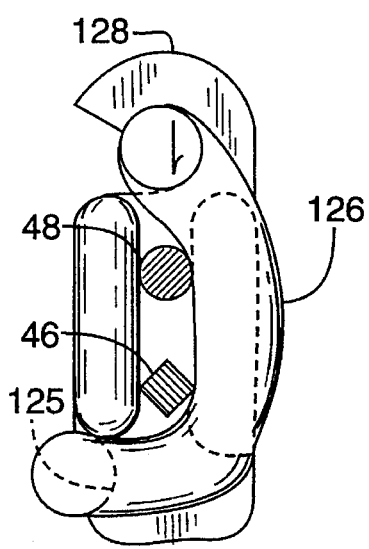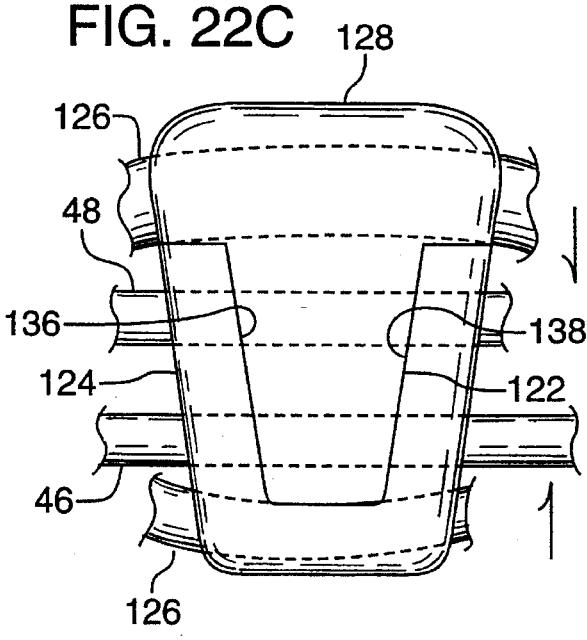

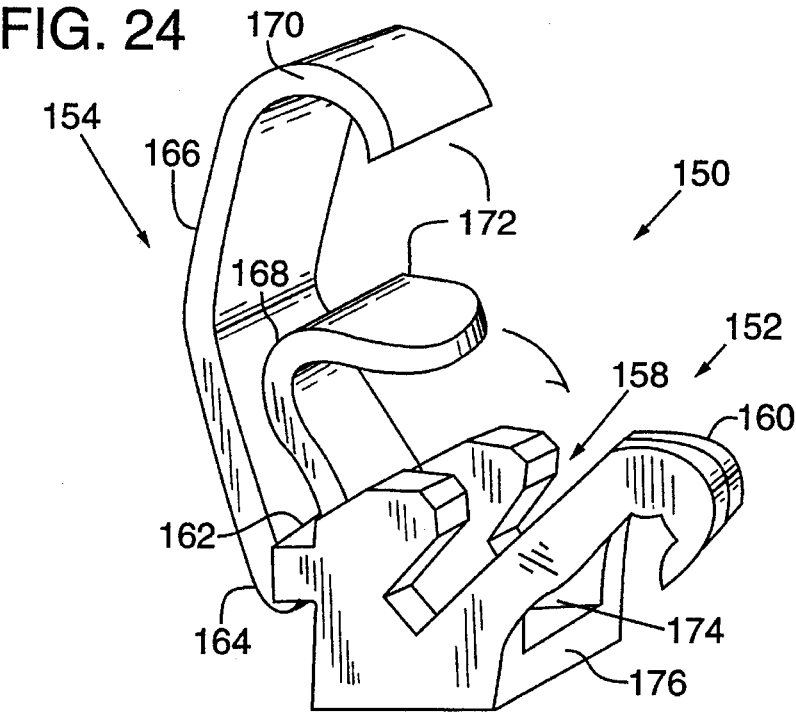
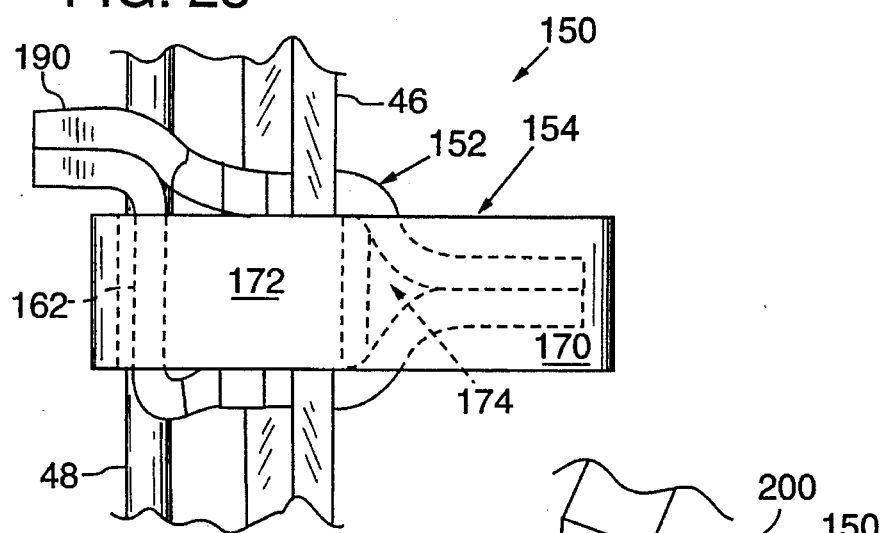
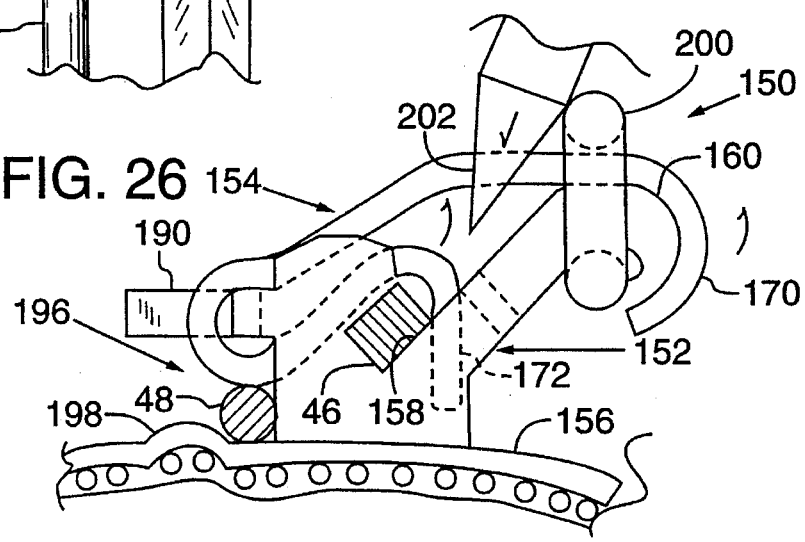

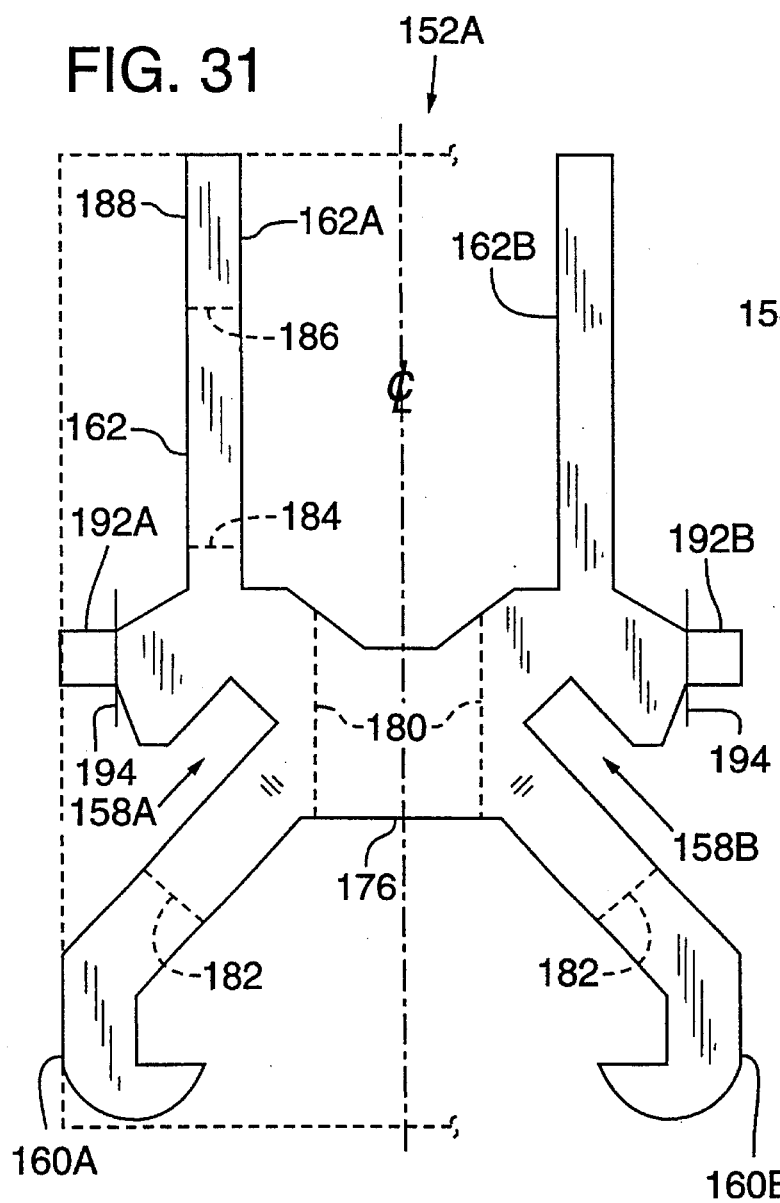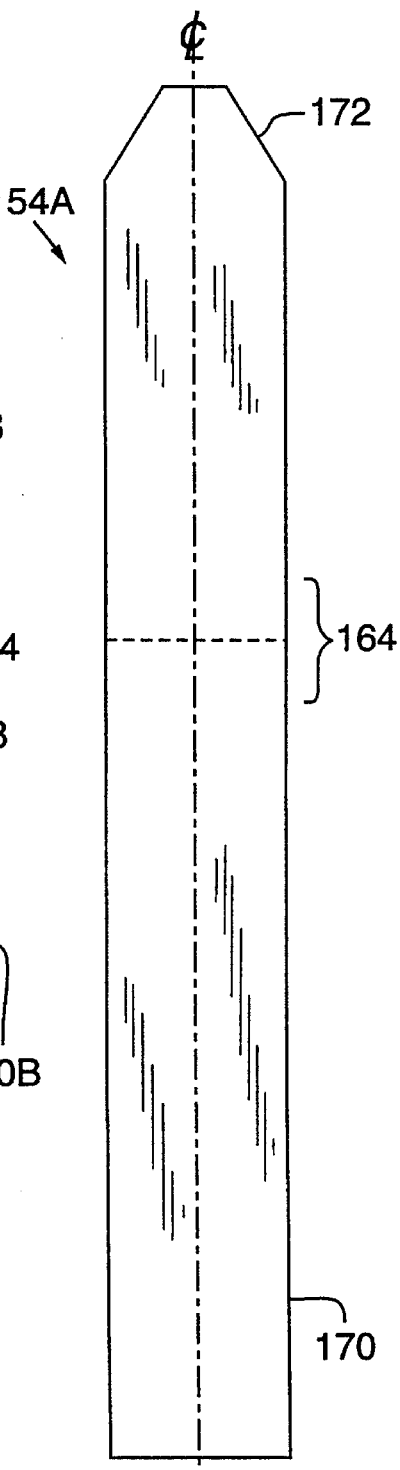

MULTIWIRE ARCH SYSTEM

RELATED APPLICATION DATA

This application is a continuation-in-part of U.S. application Ser. No. 07/842,234, filed Feb. 26, 1992, now U.S. Pat. No. 5,295,886, which is a continuation-in-part of U.S. application Ser. No. 07/684,053, filed Apr. 11, 1991, now U.S. Pat. No. 5,100,316, issued Mar. 31, 1992, which is a continuation-in-part of U.S. application Ser. No. 07/472,362, filed Jan. 29, 1990, now U.S. Pat. No. 5,011,406, issued Apr. 30, 1991, which is a continuation-in-part of U.S. application Ser. No. 07/249,453, filed Sep. 26, 1988, now U.S. Pat. No. 4,909,735, issued Mar. 20, 1990.

BACKGROUND OF THE INVENTION

This invention relates generally to orthodontic treatment and more particularly to the archwire bracket force delivery system.

Orthodontic treatment of teeth is accomplished by applying force to the teeth with a spring-resilient archwire positioned in the channels in attachments on the teeth which are called brackets. Since the beginning of orthodontics in the late 1800's, orthodontists have been pursuing the goals of increased appliance resiliency and increased appliance control.

Edward H. Angle is considered the father of modern orthodontics. Angle's U.S. Pat. No. 678,453 shows a rigid outer archwire with teeth tied to the archwire to draw them into position (FIG. 1). The bands on the teeth were attachments which were really simple cleats. In 1925 in U.S. Pat. No. 1,584,501, Angle added a rectangular slot to the bracket with wings to receive tiewires (FIGS. 2 and 3). Because the slot was perpendicular to the long axis of the tooth, it was called the edgewise appliance. The initial heavy archwire was bent to the shape of the malocclusion and was gradually straightened out. This device produced very precise control but was extremely rigid and non-resilient.

Also in 1925, Angle was issued U.S. Pat. No. 1,552,413, which disclosed a bracket designed to receive a rectangular archwire that was called a ribbon arch because the long axis of the archwire cross section was in the same plane as the long axis of the tooth. This bracket was locked with a pin which was held in place by bending the pin after it was inserted in its locking position. This bracket was later used by Spencer Atkinson and was developed into what was known as the "Universal Technique" (FIG. 4). Atkinson's art was taught in U.S. Pat. Nos. 1,821,171; 2,196,516; and 2,305,916.

This same bracket was modified by Dr. P. R. Begg and was used extensively in what is called the "Begg Technique." Begg's modifications are described in U.S. Pat. No. 3,128,553. Dr. Angle's edgewise bracket has evolved into the "Edgewise Technique" which is the most commonly used technique today.

Typically, the archwire is secured in the archwire slot using an elastic O-ring or a wire ligature wrapped around wings extending laterally on opposite sides of the slot. An edgewise bracket can be augmented to provide traction hooks while assisting in securing the archwire in the archwire slot as disclosed in U.S. Pat. No. 4,713,001 to Klein. It is also known to use a retaining spring clip over the archwire slot in an edgewise bracket as disclosed in U.S. Pat. No. 4,551,094 to Kesling; U.S. Pat. No. 4,712,999 to Rosenberg; and the ORMCO Catalog, page 27 (1992). U.S. Pat. No. 4,492,573 to Hanson discloses a bracket which has an additional slot extending transversely under the archwire slot to slidably receive one leg of a spring clip while a second or external leg extends over one side of the bracket and has a distal end that protrudes into the archwire slot to hold the archwire.

To this evolution was incorporated the use of a number of archwires beginning with relatively small diameter round wires and finishing with the large rectangular edgewise wire. This progression of archwires provided a tremendous increase in resiliency. It also forced the orthodontist to go through a number of laborious archwire changes. To further increase the resiliency of the archwires, orthodontists incorporated all sorts of geometric bends in almost every conceivable shape (FIG. 5). These bends increased the resiliency but they decreased the amount of control. One example of lack of control is what is known as a closing loop. Closing loops are used to close space. They consist of a U-shaped bend which is activated when it is spread out and held in the spread-out manner by bending the wire or tying back the wire in a step position against the molar teeth. This certainly does close space but also tips teeth rather than moving them bodily.

One of the more extreme configurations is described by Alan C. Brader in U.S. Pat. No. 3,593,421. This configuration called the multi-helical omni arch is basically an archwire with a series of coil spring bends incorporated between each teeth (FIG. 6). This certainly increased the resiliency of the archwire but it also decreased the amount of control available. To provide increased resiliency and still maintain control, orthodontists sometimes turned to multiple archwire fitting in multiple slots in the brackets. Atkinson's modifications of Johnson's ribbon arch bracket incorporating two archwires were mentioned above. This technique evolved into the Universal Technique which was used by a small but very enthusiastic group of professionals.

Another approach was described by Joseph Johnson in U.S. Pat. Nos. 1,952,320; 2,665,480 and 2,759,265. Johnson incorporated two small diameter archwires held together in a ribbon arch configuration with the long axis going through the two wires parallel to the long axis of the tooth (FIG. 7). U.S. Pat. No. 3,302,288 to Tepper discloses a another two-wire bracket arrangement using two parallel spaced apart crossbars interconnected by a rigid member.

The problem with all two wire techniques is the difficulty in putting in compensating bends. In theory, if the bracket of a tooth is put on the tooth in such a position that the channel of the bracket is in an ideal position, a straight archwire placed in this channel would reduce a tooth positioned in the ideal position. In actual practice, this does not happen. In the earlier days of orthodontics, the brackets were put on perpendicular to the horizontal plane of the orthodontic band. To compensate for the fact that this is not necessarily the ideal position, the orthodontist had to make compensating bends in the arch.

This problem was addressed by Dr. Larry Andrews by methods described in U.S. Pat. Nos. 3,477,128 and 3,660,900. Andrews attempted to position the slots in the bracket in such a relation to the base of the bracket that was applied to the tooth so that the slot assumed the ideal position in the average tooth. Since these brackets were generally put on the tooth by the orthodontist in the mouth using the orthodontist trained eye, errors in position were inevitable. Also, not all teeth are average and this also increases errors, so the orthodontist today must still finish cases with compensating bends.

Another twin arch approach that is very interesting is described by J. D. Berke in U.S. Pat. Nos. 2,406,527 and 2,705,367. Berke described a bracket which is essentially a button with two channels separated by the body of the bracket (FIG. 8). Two archwires were connected by rigid connectors between the two teeth. In one situation, the connectors were fixed and in another situation, they were slidable. The archwire was connected to the tooth by pulling the two archwires away from each other and snapping the two archwires over the bracket. The archwires returning to shape aligned the tooth. The fact that the connectors were rigid made this system very difficult to use in actual practice. It was never produced in any significant quantity commercially.

Another attempt attaining precision with two wires was described by Northcott in U.S. Pat. No. 3,775,850. Northcott connected two and three archwires together with interarch connectors (FIG. 9). These connectors were rigid cast or brazed metal, both fixed and slidable. This rigid system was tied into corresponding slots in the labial bracket. Like Andrews, Northcott tried to eliminate the necessity for compensating bends by building the archwire slots in such a position that they were in the ideal position in the average tooth. Again, this had the problems of the Andrews system. Teeth are not always average and the operator cannot always get the bracket on the tooth in the ideal position using his eye alone. A disadvantage of Northcott's system over Andrews' system is the complete inability to put any compensating bends in the arch if the need arises.

The recently introduced NiTi wires, which are an alloy of nickel and titanium, are extremely more resilient than stainless steel. The disadvantage of these wires is the inability to readily bend the archwires. Nickel titanium archwires are usually held into shape and heat treated. This is commonly done today in the factory using preformed shapes. No compensating bends are really possible.

Dr. Alexander J. Wildman has previously developed lingual orthodontic methods and brackets as described in U.S. Pat. Nos. 3,748,740; 3,780,437; 3,842,503; 3,854,207; 4,443,189; and 4,494,931. U.S. Pat. No. 4,443,189 mentions the possibility of mounting a second or auxiliary archwire on the bracket but requires threading the second wire through the slot so its use is limited to the attachment of auxiliaries.

Wildman has also taught a way to very accurately place the brackets on the teeth using what he calls the direct-indirect technique in U.S. Pat. No. 4,909,735. Wildman also teaches a method of custom heat treating the nickel titanium archwires into an ideal shape for each individual patient, in U.S. Pat. Nos. 5,011,406; 5,100,316; and Ser. No. 07/842,234, filed Feb. 26, 1992, now U.S. Pat. No. 5,295,886, incorporated herein by this reference. This shaping method opens up a number of possibilities for very complicatedly-shaped archwires which would not need compensating bends placed by the operator.

Dr. Wildman also published ideas for advanced lingual orthodontia including a compact lingual bracket (FIG. 10) in "The Future of Lingual Orthodontics," *Orthodontics: Evaluation and Future,* Proceedings of the International Conference of the Orthodontic Dept. of Univ. of Nymegen, The Netherlands, Oct. 22–24, 1987, pp. 261–280 (1988). None of these references disclose an effective way to use multiple archwires.

Accordingly, a need remains for a multiple archwire orthodontic method and bracket that overcomes the deficiencies of the prior art.

SUMMARY OF THE INVENTION

It is, therefore, an object of the invention to provide optimum archwire bracket systems designed to take advantage of the new setup and archwire forming technology in multiple archwire orthodontics.

Another object of the invention is to enable multiple archwires to be used more easily and with more versatility.

A further object of the invention is to improve both the precision and resilience of multiple archwire systems.

An additional object is to provide an improved ligature-less lingual orthodontic bracket.

One aspect of the invention is an improved multiwire orthodontic method which uses, in labial applications, either an improved Berke bracket or a multiwire edgewise bracket. The labial multiarch brackets have in common an ability to receive and hold two archwires in slots spaced occluso-gingivally along opposite sides of the bracket. The slots are oriented so that the occluso-gingivally spaced archwires are inserted at nonparallel angle, preferably about 90° to one another. In a labial bracket this angle is preferably about 45° to an occluso-gingival axis of the body of the bracket. The slots are sized to receive and securely hold a cross-sectional dimension of an archwire in a base portion of the slot and are funnel-shaped to guide the archwires gradually into the base portions of the slots to be seated therein. In the multiwire edgewise embodiment of this bracket, a third, central slot is formed for receiving an edgewise archwire between the occluso-gingivally spaced archwire slots.

A second aspect of the invention is an interarch connector which, by spanning the two occluso-gingivally spaced archwires, can be used to urge the archwires toward one another into the slots on opposite sides of the bracket and to retain them seated in the base portions of the slots. In its simplest form, the interarch connector can be a resilient elastomer multi-tubular member through which the archwires are threaded between adjacent brackets. Other forms can be made of flat or round wire springs. The interarch connector has two holes (or three in the edgewise embodiment) for receiving the two occluso-gingivally spaced archwires. These holes are spaced center-to-center a distance approximately equal to or slightly less than the center-to-center spacing between the base portions of the occluso-gingivally spaced slots on opposite sides of the bracket. Alternatively, the multi-tubular interarch connector can be formed of a rigid material with the occulsal and gingival channels open on one side, which can be curved to shape or control the archwire transversely of its length. As a further alternative, the interarch connector can be a two-part interengaging sliding structure arranged to retain two arch wires in a slot having a variable length for urging the wires together as the two parts of the connector are pulled toward one another by an elastic or locked by a spring clip or bail.

In combination, the multiarch bracket and interarch connector exert force on the brackets, and thereby on the teeth, with gradually increasing precision as the occluso-gingivally spaced archwires are urged by contraction of the interarch connector toward one another into the base portions of the spaced slots. Because the slots are positioned at a nonparallel angle to one another, the archwires received therein are urged deeper into the slots with a force component oriented in a direction transverse to the direction of contraction of the interarch connector. The slots have an entrance portion that is wider than the cross-sectional dimension of the archwire. This entry permits the archwires to be partially engaged in the bracket notwithstanding differences between the bracket position (mounted on a maloccluded tooth) and the archwire (shaped to move the tooth toward an ideal arch position). As the archwires migrate toward the base portions of the slots, the sidewalls of each slots converge or taper toward a parallel relationship. This shape gradually moves the archwires into tightly controlled positions seated in the base of each slot. An interarch spacer or stiffener can also be used to assert simultaneous control over the multiple arch wires.

A further aspect of the invention is a multi-arch lingual orthodontic method and bracket which utilize the foregoing principle. The lingual bracket is preferably a ligatureless or automatic type bracket formed to provide two archwire slots spaced occluso-gingivally along opposite sides of the bracket and oriented at a nonparallel angle as summarized above. The bracket has a body which is shaped to form a base that can be affixed to a tooth surface via a bonding pad, a central arch wire slot oriented at about a 45° angle to the base, a hook extending at about a 45° angle from the base along one side of the central archwire slot, and a hinge formed a side of the central archwire slot opposite the hook. The bracket also has a spring clip closure member formed by a narrow flat spring which is multiple-curved to form a first bend around the hinge of the bracket body, a second bend in a direction opposite the first bend and positioned to lock over the hook of the bracket, and a third bend in the same direction as the second bend and nested within the second bend so as to extend into the central archwire slot to retain the archwire therein when the second bend is locked over the hook. In the overall bracket structure, when mounted on a bonding pad, a notch is formed between the hinge portion of the lock spring, the adjoining side of the bracket body, and the bonding pad, which notch can receive an auxiliary arch wire. A bump can be formed in the bonding pad alongside this notch to tighten the shape of the notch to more securely seat the auxiliary archwire therein.

The foregoing and other objects, features and advantages of the invention will become more readily apparent from the following detailed description of a preferred embodiment of the invention which proceeds with reference to the accompanying drawings.

BRIEF DESCRIPTION OF THE DRAWINGS

FIG. 11 is a side elevation view of an edgewise-type labial orthodontic bracket for a multi archwire configuration in accordance with the invention.

FIG. 12 is a side elevation view of an interarch connector for use in accordance with the present invention.

FIG. 14 is an elevation view of an alternate form of interarch connector formed used using a resilient flat spring.

FIG. 15 is another alternative form of interarch connector made from resilient round wire.

FIG. 16 is an end elevation view of a flat interarch spacer in accordance with the invention.

FIG. 22A is an exploded side elevation view of a sliding-type interarch connector according to an alternative embodiment of the invention.

FIG. 22B is an assembled side elevation view of the interarch connector of FIG. 22A.

FIG. 22C is a front elevation view of the connector of FIG. 22B.

FIG. 23 is a side elevation view of the upper part of the interarch connector of FIG. 22A with an alternative lock spring closure.

FIG. 24 is a perspective view of a lingual orthodontic bracket in accordance with the invention, with its lock spring shown hinged to an open position.

FIG. 25 is a plan view of the bracket of FIG. 24, shown with the lock spring closed over a first archwire and a second archwire received in a recess between the lock spring hinge and bonding pad along the occlusal side of the bracket body.

FIG. 26 is a side elevation view of the bracket of FIG. 25.

FIG. 31 is a plan view of a flat metal sheet patterned to form the body portion of the bracket of FIGS. 24–26.

FIG. 32 is a plan view of a flat spring patterned preparatory to forming the spring portion of the bracket of FIGS. 24–26.

DETAILED DESCRIPTION

Figure 1:
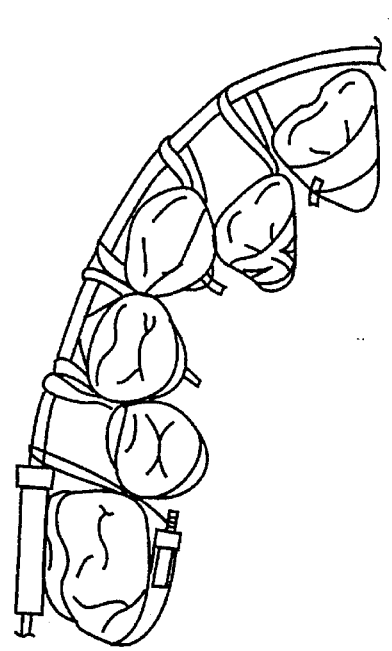
FIGS. 1–10 are drawings of prior art orthodontic devices and techniques.
Figure 2:
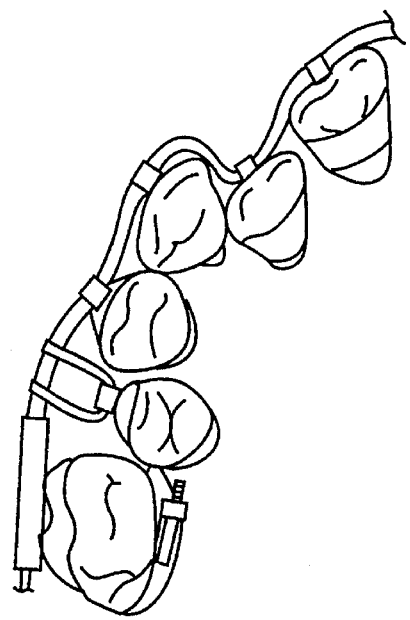
Figure 3:
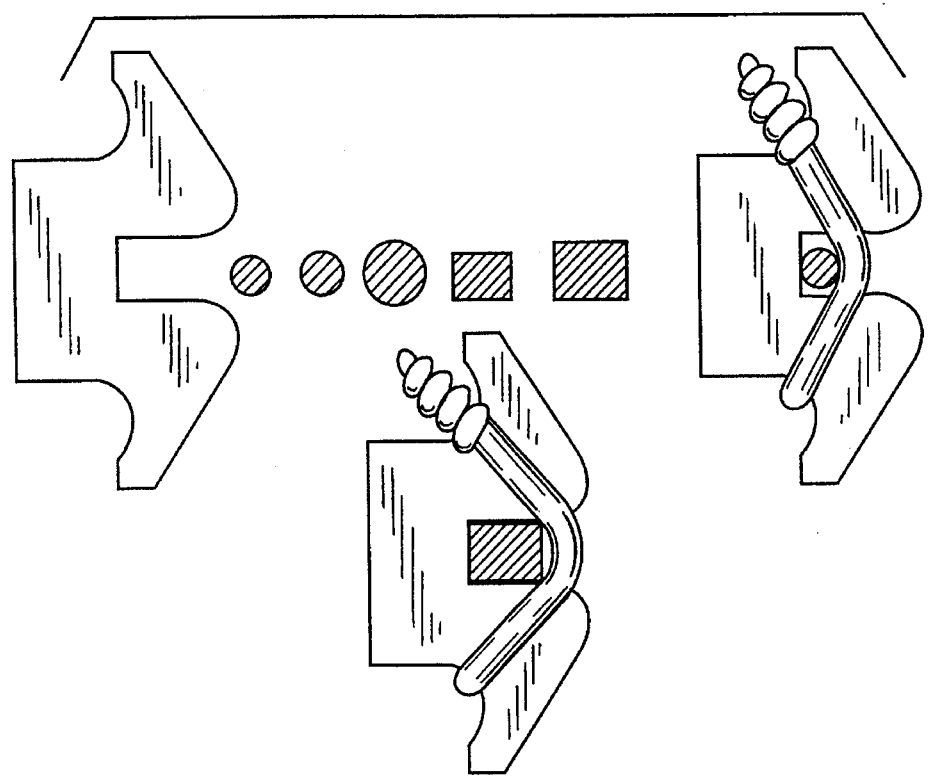
Figure 4:
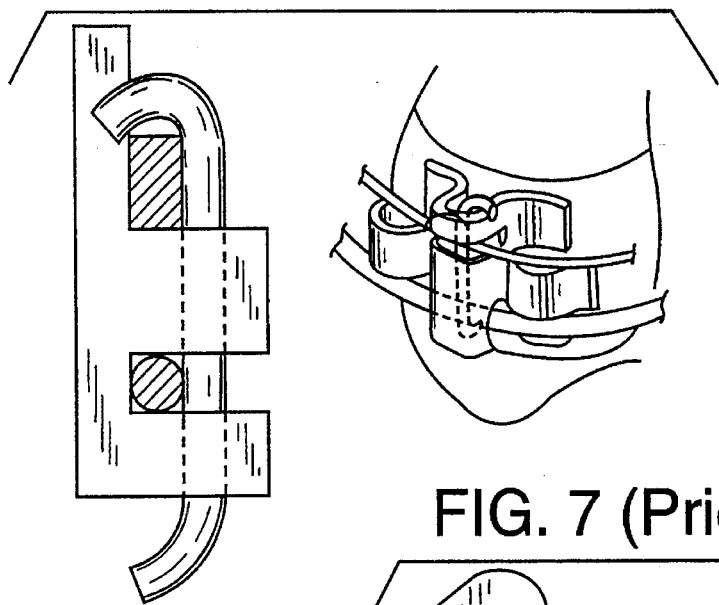
Figure 7:
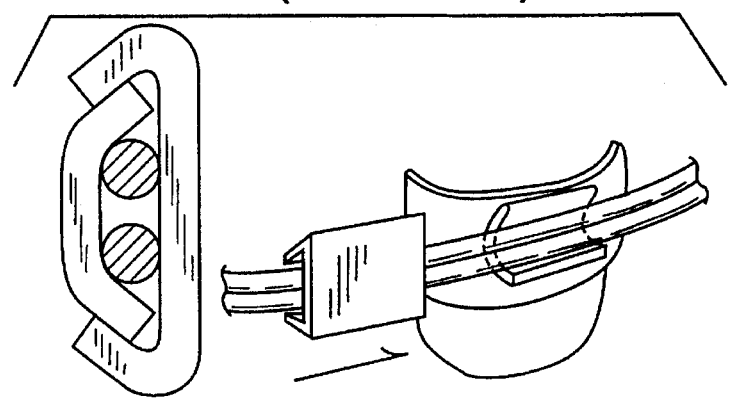
Figure 8:
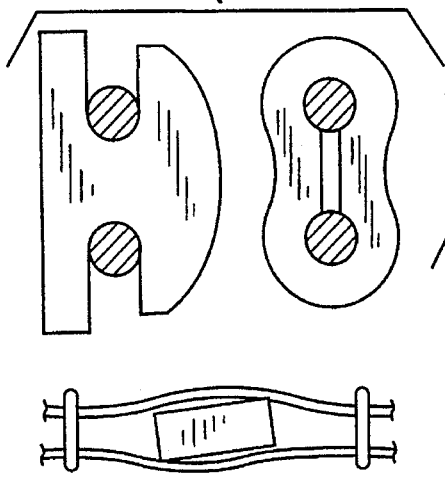
Figure 9:
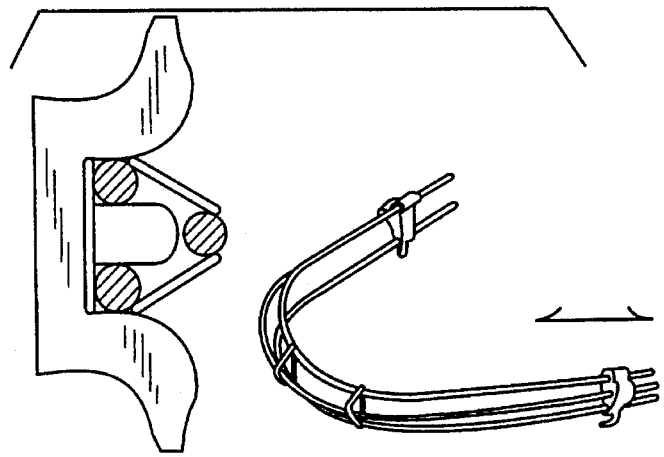
Figure 5:
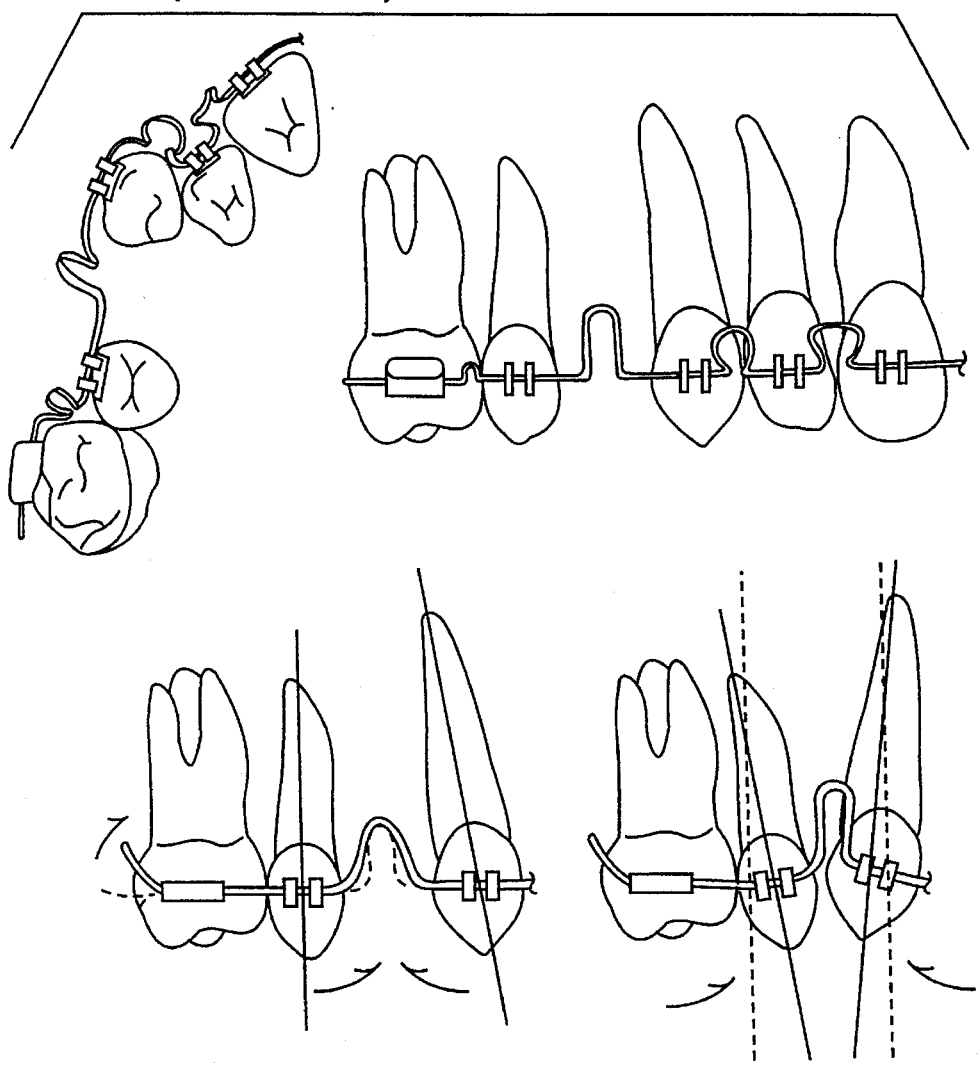
Figure 6:
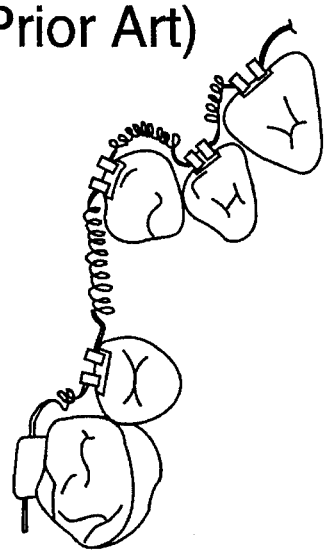
Figure 10:
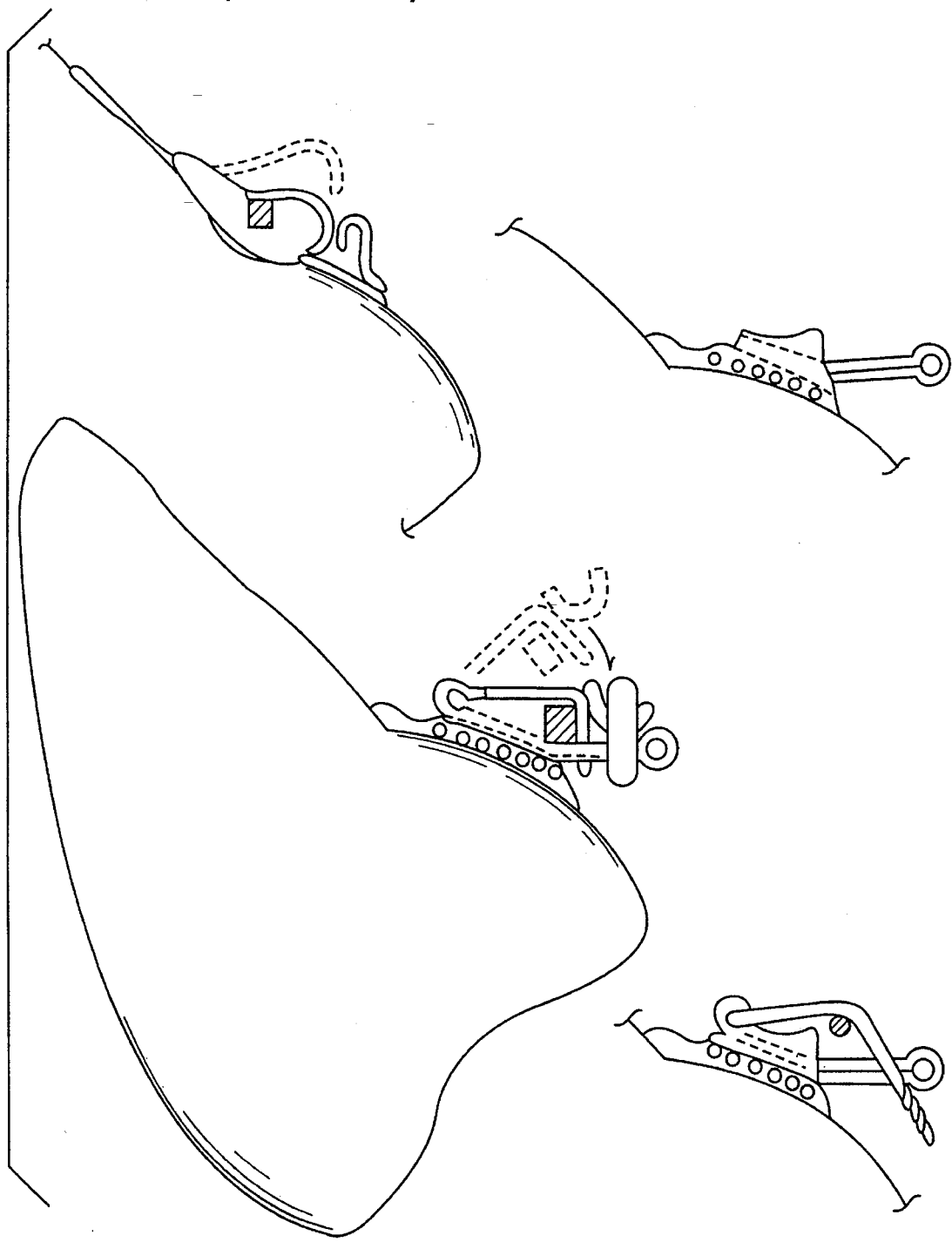
Figure 13:
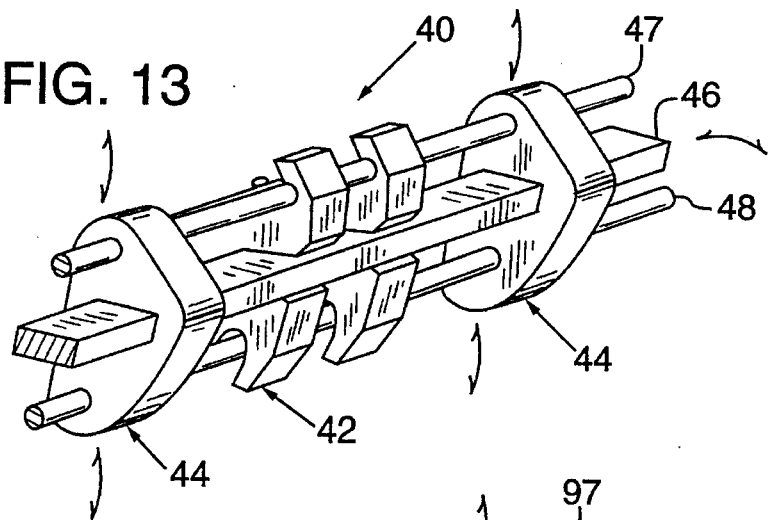
FIG. 13 is a perspective view of a multi arch setup utilizing the bracket of FIG. 11 and two interarch connectors of FIG. 12.

FIGS. 11–13 respectively show a multi arch edgewise bracket 42, and elastomeric interarch connector 44 and a multiwire arch system 40 in accordance with the invention. In this embodiment, three archwires can be used: a central archwire 46 having a rectangular cross section, and two auxiliary arch wires of circular cross section, which are identified herein for convenience as the occlusual archwire 47 and the gingival 48. Bracket 42 is an improved edgewise bracket having a base portion 50 for mounting the bracket on a tooth via a bonding pad (not shown); a central archwire slot 52 for receiving rectangular archwire 46; and a pair of oppositely-directed wings 54. In the conventional edgewise bracket, as exemplified in Lewis U.S. Pat. No. 2,854,747, a large semicircular opening is typically provided under each of the hooks to permit easily placement and removal of elastomer O-rings, and the base of the bracket typically has parallel vertical sides beneath the wings.

In the improved edgewise bracket 52, the base 50 and the undersides of wings 54 are shaped to form slots 56 sized to receive and securely hold the cross-sectional dimension of archwires 47, 48 in a base portion 58 of the slot and are funnel shaped in a lead-in portion 60 of the slot to guide the archwires gradually into the base portions of the slots to be seated therein. The base portion has short sections of parallel sidewalls that are spaced apart to provide a slidable tolerance fit to the auxiliary archwires. For example, for a circular cross section archwire having a diameter of 0.016 inch, the spacing between the sidewalls in base portion 58 of the slot should be about 0.0165 inches. The lead-in portion 60 of the slot is wider than the base portion of the slot and is defined by sidewalls along the base 50 of the bracket and the underside 62 of the wings that are angled or tapered convergently toward the parallel sidewalls of the base portion of the slot to guide the archwire into the base portion. Thus, it can be seen comparing the improved edgewise bracket 42 with the conventional edgewise bracket as exemplified by Lewis, that the sides of the base portion of the bracket are not vertical parallel surfaces but have an inward taper forming a notch beneath the wings 54, which notch defines the base portion of the auxiliary archwire slots on opposite sides of the bracket 42.

FIG. 12 shows the shape of an elastomer interarch connector 44 configured to receive three archwires 46, 47, 48 in the same relative positions as when such archwires are seated in bracket 42. The interarch connector is made of molded polyurethane having a central rectangular tubular passageway for receiving archwire 46 and a pair of circular passageways spaced apart about the central passageway for receiving archwires 47, 48. The circular passageways or holes are spaced center-to-center a distance approximately equal to or slightly less than the center-to-center spacing between the base portions of the auxiliary archwire slots 56 on opposite sides of the bracket 42. The relative positions of the holes can be varied to change the amount of force applied to retain the archwires in the slots.

FIG. 13 shows the manner of use of bracket 11 and interarch connectors 44 in a multi-arch system 40. The brackets 42 are affixed to the patient's teeth, using known methods. The brackets are positioned using my setup method and the individual archwires are preformed to an arch form customized to the patient using the techniques described in prior U.S. Pat. Nos. 4,909,735; 5,011,406; and 5,100,316 and Ser. No. 07/684,053, incorporated herein by reference. This method enables each archwire to be preformed identically to the ideal arch form for the patient. The archwires 46, 47, 48 are then threaded through multiple interarch connectors 44 and the interarch connectors are spaced apart as needed along the archwires, outside the patient's mouth. Then, the assembled archwires and connectors are positioned in the brackets with the central archwire 46 received in slots 52 while the auxiliary archwires 47, 48 are spread apart to clear the wings 54 of the bracket. The resiliency of the archwires and the interarch connectors permits the auxiliary archwires 47, 48 to be spread apart when being placed and then draws the archwires toward one another to be guided inwardly by the lead-in portions of the slots 56 until seated in the base portions 58 thereof.

The multi-arch system 40 provides several advantages. One advantage is that adding auxiliary archwires increases the torque arm of force applied to the tooth over that available from conventional edgewise archwire systems. Another is that the interarch connector will seat the central archwire and the auxiliary archwires in their respective slots without need for a ligature of any type, such as a conventional elastomer O-ring or steel tie. Thus, this system makes the edgewise bracket into a ligature-less bracket without the complications of a lock mechanism in the bracket itself. The stiffness of the overall system can be modified by using or leaving out the central archwire as desired by the treating orthodontist.

FIGS. 14–18 show various alternative forms of interarch connectors and spacers. FIG. 14 shows an interarch connector 64 formed by a flat spring which is folded to provide a central U-shaped section 66 for receiving the central archwire and a pair of circularly-folded distal end portions 67, 68 for receiving the auxiliary archwires 47, 48. The distal end portion 67, 68 are connected to the central portion 66 by means of semicircular folds 63, 65. A suitable material for this purpose is 301 full hard stainless steel.

FIG. 15 shows an alternative interarch connector 70 formed by a circular cross section spring-type wire, suitably made of 302 stainless steel, which is coiled at its distal ends to form short helical loops 77, 78 for auxiliary archwires 47, 48. A central portion of the wire is wound several times to form a generally rectangular-shaped enclosure 76 for the central archwire 46 and is connected to the distal end portion 77, 78 by means of semicircular or circular loops 73, 75. The distal end portion 77, 78 would ordinarily be formed so that they are biased toward the central portion 76 to apply a seating force to the auxiliary archwires 47, 48.

FIG. 16 shows an interarch spacer 80 having a central passageway 86 which is rectangularly-shaped to slidingly receive archwire 46. A pair of slots 87, 88 are formed in opposite sides of spacer 80 for receiving auxiliary archwires 47, 48 and defining a minimum spacing between the auxiliary archwires. This spacer can be used in conjunction with one of the interarch connectors 44, 64, 70.

The interarch spacer can be formed of a thin metal sheet material such as of appropriate stainless steel which has been stamped or chemically etched to the desired configuration. Alternatively, the spacer can be formed so as to be thicker along the long axis of the channels by extrusion of a suitable alloy such as inconol, or a hard plastic such as polycarbonate or polysulfone.

Figure 17:
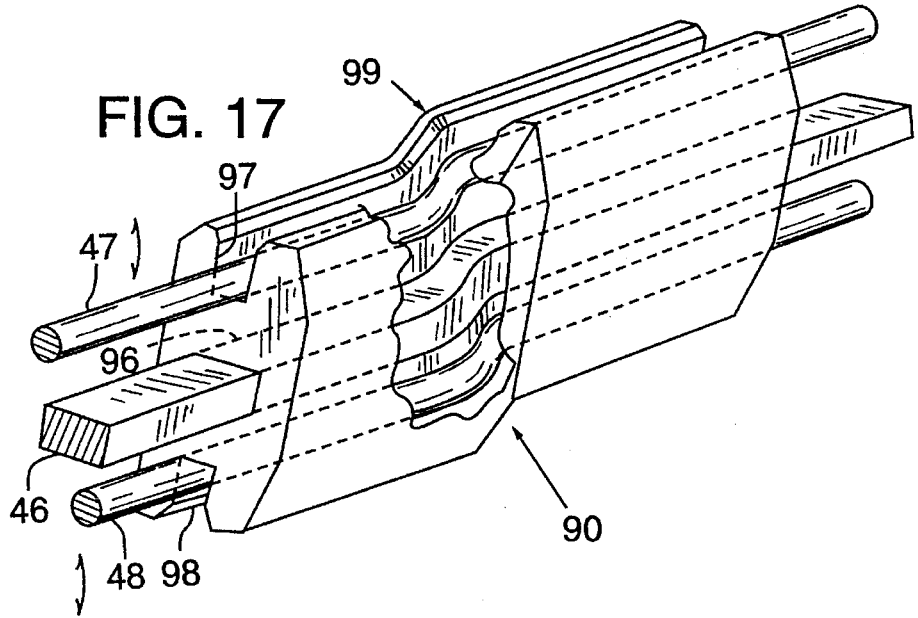
FIG. 17 is a perspective view of an interarch spacer with segment-forming channels.

FIG. 17 shows an archwire segment-forming appliance 90 extending the principles disclosed and claimed in my prior application Ser. No. 07/842,234. This appliance has a cross-sectional shape similar to that of spacer 80, including a central passageway 96 for archwire 46 and oppositely-directed channels 97, 98 for wires 47, 48. It typically has a longer length in the lengthwise-dimension of the archwires. In use, appliance 90 serves to stiffen a segment of the archwires and can be used to impart localized bends to the archwires, in addition to the spacing function of the appliance. Appliance 90 can be formed by molding plastic or by extruding inconol in the desired shape. If made of plastic, the appliance would be molded with any bend formed in the part as molded. In the case of an extruded inconol part, the bend 99 can be formed in the part after extrusion. To do this without crimping the channels closed, dimensional brass wires having the same shape and cross-sectional dimensions as the channel and slot are inserted into the channels and slot, the part within the bend to form the desired bend 99, and after bending, the brass wires are removed by chemical etching. Then, the NiTi wire can be threaded into slot 96 and inserted into channels 97 and 98 at a temperature at which the wire is readily bendable so that the wires will readily assume the shape of the slot and channels.

Figure 18:
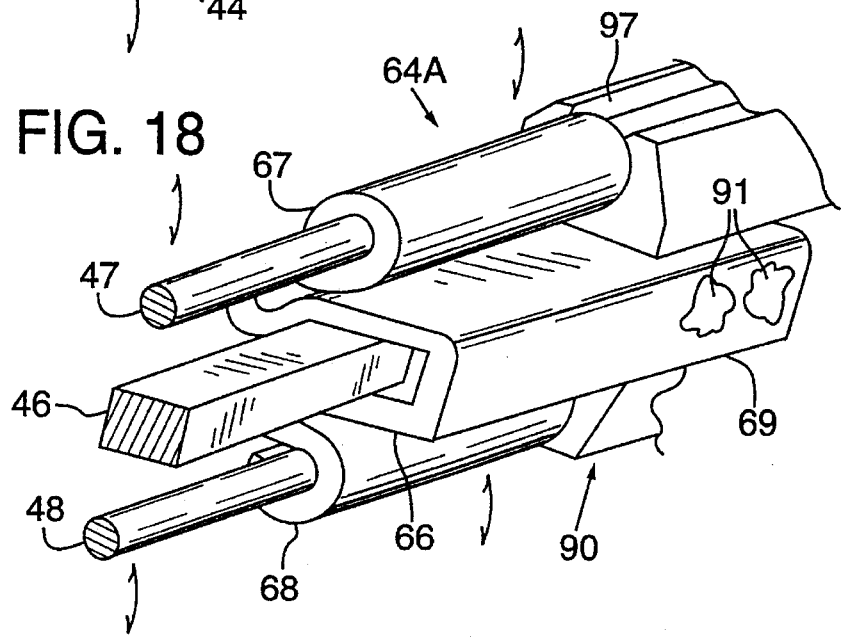
FIG. 18 is a perspective view of a combination of an interarch spacer as shown in FIGS. 16 and 17, together with a flat spring-type interarch connector of the type shown in FIG. 14.

FIG. 18 shows an interarch connector 64A which is a variation of connector 64 shown in FIG. 14, connected end-to-end with appliance 90. Connector 64A includes all of the structure previously described in connector 64. In addition, the central portion 66 includes a lengthwise extension or welding tab 69 which extends a short distance alongside appliance 90 and can be affixed thereto by means of spot welds 91.

Figure 19:
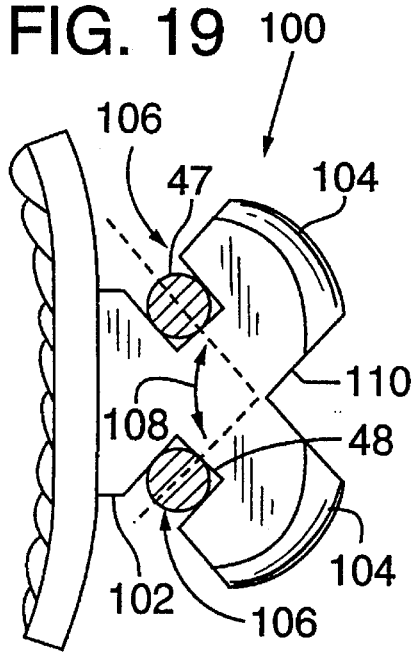
FIG. 19 is an end elevation view of a two-wire labial bracket according to the invention.
Figure 20:
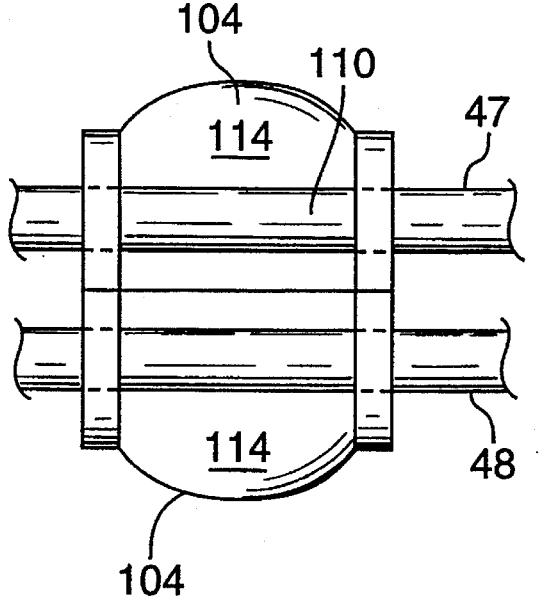
FIG. 20 is a front elevation view of the bracket of FIG. 19.
Figure 21:
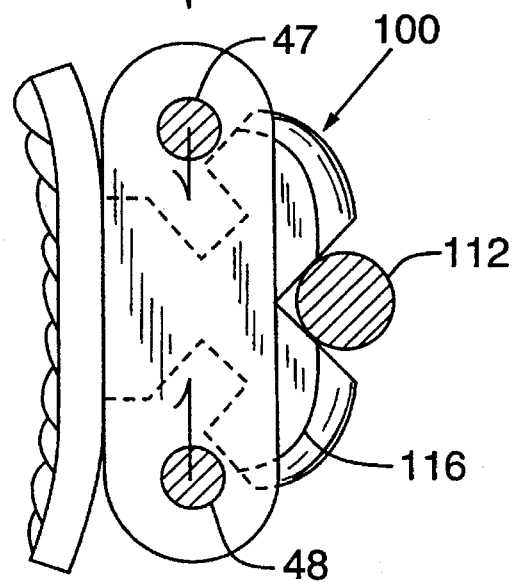
FIG. 21 is an end elevation view of the combination of the bracket of FIG. 19 with a two-wire interarch connector according to the invention.

FIG. 19 shows an alternative form of multiwire labial bracket 100. This bracket enables two archwires to be secured in generally the same manner as described by Berke U.S. Pat. No. 2,406,527, but with several improvements. In the Berke bracket, the two archwires are inserted occluso-gingivally in the same plane, that is, the archwire slots are oriented at an angle of 180° to one another. Consequently, the Berke bracket presents no resistance to the archwires coming out of the slots, for example, if the bracket is at an angle to the overall direction of the archwires, as illustrated in the Berke patent. In contrast, bracket 100 has a body 102 and wings 104 formed to orient the slots 106 so that the direction of the insertion of the archwires 47, 48 therein, as illustrated by dashed lines, is at a nonparallel angle 108, a range of 90°–100°. This is the same relationship as slots 56 in the multiwire edgewise bracket 42 shown in FIG. 11. In Berke, the openings of the archwire slots do not oppose relative rotation of the bracket and archwire. In contrast to Berke, in brackets 42 and 100, at least one of the slots 56, 106 will present a closed face to resist the archwire coming out of the slot. Bracket 100, unlike bracket 42, does not have a central archwire slot. Instead, it has a V-shaped notch 110 which can served as a guide for elastemer thread 112 to be tied from one bracket to another over several brackets to apply a contractive force along the lengthwise dimension of the archwires, or for an additional archwire, as illustrated in FIG. 21. Referring to FIG. 20, the wings 104 can have lip bumpers 114, for example, formed of plastic inserts mounted on their labial surfaces.

Referring to FIG. 21, the bracket 100 and archwires 47, 48 are shown together with a two-wire elastomer interarch connector 116, shown in a stretched condition for pulling the archwires together along the undersides of wings 104 of the bracket 100. Flat spring and wire interarch connectors similar to those shown in FIGS. 14 and 15 can alternatively be used, as can the spacer of FIG. 16 and a segment-forming appliance like that of FIG. 17.

FIGS. 22A–22C show an alternative form of interarch connector 120 comprising two parts 122, 124 which can be held together by elastomer O-ring 126. In general, parts 122, 124 are structured to nest together in a sliding interengaging relationship to retain two archwires in a slot having a variable length for urging the wire together as the two parts of the connector are pulled toward one another by elastic 124. The upper part 122 has a hook 128 at its upper end having an opening 130 for receiving a loop of the elastomer O-ring, and has a downwardly-opening U-shaped portion with an elongate slot 132 for receiving archwire 40, 48. The lower part 124 has a generally U-shaped body defining an upwardly-opening slot 134 for receiving archwire 46. Slot 134 can be wider than slot 132. As seen in FIG. 22C, the slot-forming portion of the upper part 122 is tongue-shaped and the slot forming portion of lower unit 124 is fork-shaped, with a pair of legs 136, 138 spaced apart and shaped to interfit in complementary fashion with the upper part 122.

When the upper and lower parts 122, 124 are nested together with the archwires 46, 48 positioned within the slots, the parts are squeezed together by extending the O-ring 126 lengthwise from the upper part around the archwires to the underside of the lower unit, which preferably has a notch 125 formed therein. Alternatively, referring to FIG. 23, the upper part 122 can be provided with a leaf spring closure member 140 which is hinged on hook 128 so as to pivot between an open position as shown in solid lines in FIG. 23 and a closed position as shown in dashed lines to secure part 122 within part 124. The leaf spring has a slot 142 formed at one distal end, which slot is sized to receive hook 128. The hook is semicircular to provide an opening 144 for receiving either distal end of closure 140, or the thickness of O-ring 126. The opposite distal end of closure member 140 can be curved to engage around the lower surface of lower part 124 and, optionally, can have a recurved lip 146 to provide a lead-in for snapping the closure member into place around the lower part 124.

FIG. 24 shows a perspective view of a multiarch lingual bracket 150 which can be used to apply the foregoing techniques in lingual orthodontia. It can also be used in single wire lingual techniques. Bracket 150 comprises a body portion 152 and a spring clip closure member 154. The bracket body 152 is shaped to form a base 176 that can be affixed to a tooth surface via a bonding pad 156 (FIG. 26). The body is formed to provide a central archwire slot 158, oriented at about a 45° angle to the base, for receiving a primary archwire 46 of rectangular cross section, as shown in FIG. 26. Along one side of the body a hook 160 is formed so as to extend at about a 45° angle from the base along one side of the archwire slot. On the opposite side of the body from hook 160, a transversely-extending hinge 162 is formed for pivotally mounting the closure member 154. The spring closure member is formed by an elongate flat spring member which is bent to form a U-shaped bend 164 around hinge member 162 and to provide an outer leg 166 and an inner leg 168. The outer leg is of sufficient length to extend past hook 160 and has a curved distal end 170 which is shaped to fit conformably over hook 160 when the closure member is in the closed position as shown in FIG. 26. The inner leg 168 of the spring closure member is shorter than the outer leg and has a distal end portion 172 that is likewise bent downwardly but positioned to protrude into the archwire slot 158 to secure the archwire 46 therein. Referring to FIG. 25, the body 152 of the bracket is formed with an opening 174 alongside the archwire slot between the archwire slot and the hook 160.

FIGS. 31 and 32 show the body and closure member at an intermediate stage of fabrication. The closure member begins, as shown in FIG. 32, as a flat strip 154A of 301 full hard stainless steel about 0.010 inches thick and has its corners trimmed at one end to form the archwire slot closure end 172. The bend which forms a U-shaped bend 164 is indicated by a dashed line extending across the strip. The closure member is pre-bent to its final form prior to assembly on the bracket body. Conventionally spring-bending techniques are used to form the spring as shown and described with reference to FIGS. 24 and 26.

FIG. 31 shows a stamped or chemically etched flat member, formed of 17-7 condition A stainless steel of 0.012 inch thickness, patterned substantially as shown to scale in FIG. 31 to form the various elements of the body 152. The body has a base 174, which will be affixed to a bonding pad, and two side portions 160A, 160B, respectively containing slot portions 158A, 158B, which are formed by bending opposite sides upward about bend lines 180. Opposite sides 160A, 160B will ultimately be folded together about gradual fold lines so that end portions meet at approximately dashed lines 182 to form hook 160. The hinge is formed by bending either one of legs 162A or 162B along bend lines 184, 186 until a distal end portion 188 contacts the other side portion 162B. These portions are then welded together, as are the portions 160A, 160B which form the hook 160. The body 152 and closure member 154 are then assembled by looping strip 154 around the hinge 162, pushing end portion 170 around hinge 162 and wrapping it over the top of hook 160. A distal end portion of strip 162B extends past the end portion 188 and this can be cut off, leaving a tie hook 190. Positioning tabs 192A, 192B are provided on intermediate part 152A to provide a symmetrical rectangular shape to facilitate fitting the part into a tooling pocket for bending, and these are cut off along lines 194 once the part is assembled.

Referring to FIG. 26, the body 152 is mounted on a bonding pad 156. The overall configuration of the body 152, bend 164 of the closure member 154 and the bonding pad naturally forms an auxiliary archwire slot 196, for receiving an archwire 48. The shape of the auxiliary archwire slot 196 can be further controlled by dye stamping a bump 198 into the bonding pad when the bonding pad is formed. Alternatively, bump 198 can be formed in the bonding pad after the bracket body is affixed thereto. Ideally, when the primary archwire 46 is positioned in the archwire slot, the closure member will lock easily down over the hook 160. Seldom, however, are circumstances ever ideal. Often, the archwire is only partially gauged in the archwire slot and so that closure member will not be fully seatable over hook 160. In this situation, an elastomer O-ring 200 can be fit over the hook 160 and the distal end 170 of the closure member to force the closure member toward a locked position and hold it there until the archwire gradually seats in the archwire slot 158, at which time the closure member can be locked. To open the bracket 150, the O-ring 200 is removed and the tip 202 of a conventional dental explorer can be inserted in the space between the leg 166 of the closure member and the body of the bracket and pried upward to release distal end 170 of the closure member from hook 160.

Figure 27:
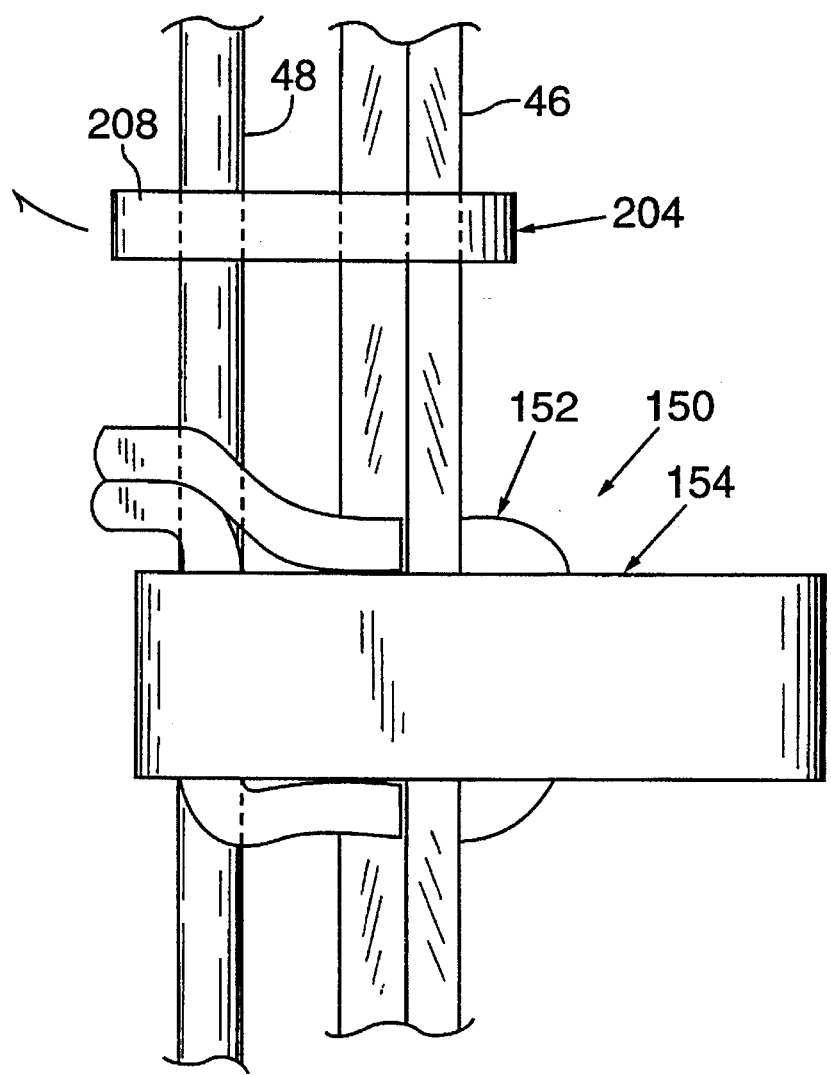
FIG. 27 is a view similar to a view of FIG. 25 showing a clamping type interarch connector used to secure the second archwire in place in accordance with the invention.
Figure 28:
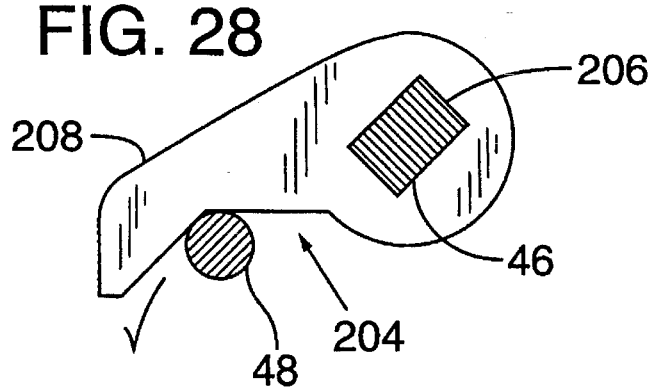
FIG. 28 is a side elevation view of the interarch connector of FIG. 27.

If an auxiliary archwire 48 is used in the bracket system of FIGS. 24–26, it can be locked in place by means of a suitable form of interarch connector as shown in FIGS. 27 and 28. This interarch connector 204 has a generally teardrop shape as shown in FIG. 28 with a rectangular slot 206 in the larger or head end, for receiving rectangular archwire 46, and a hook or spur 208 at the opposite end having a concavely-curved underside for clamping auxiliary archwire 48 against the bonding pad.

Figure 29:
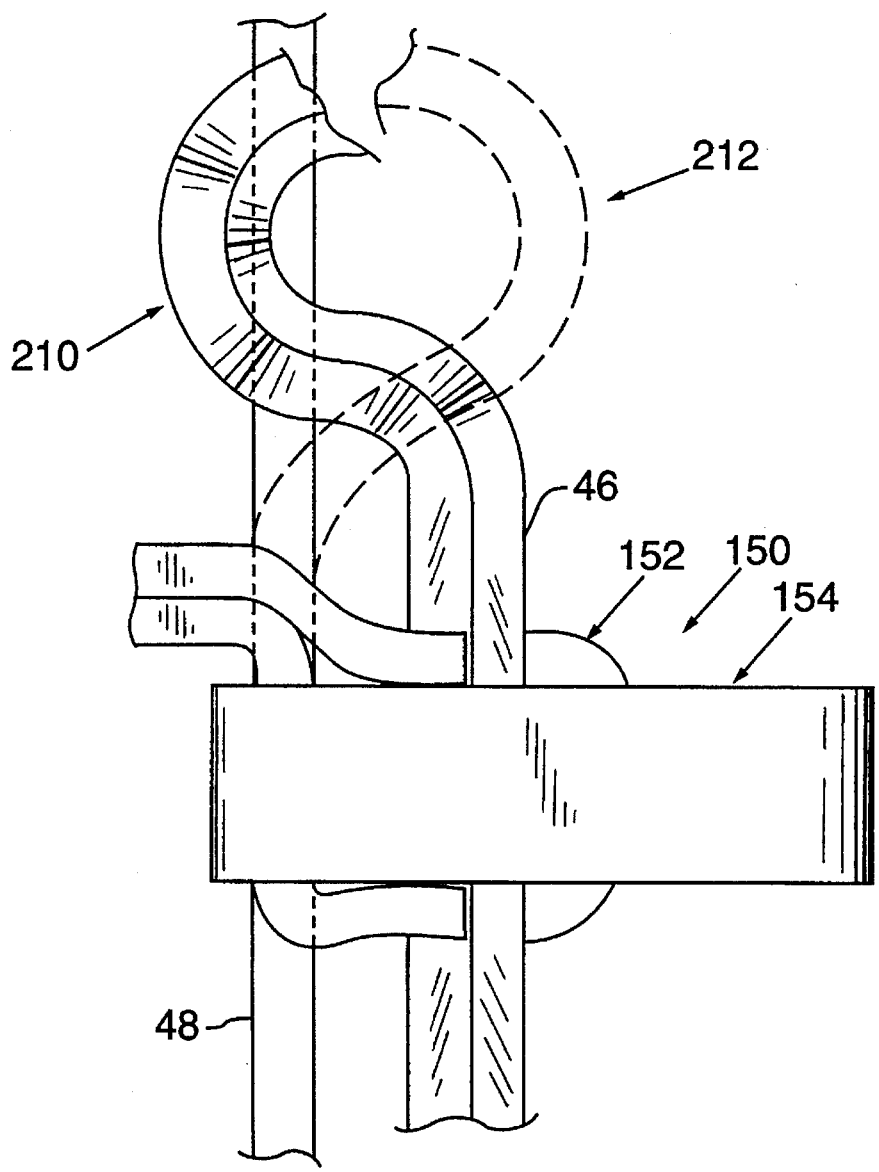
FIG. 29 is a view similar to FIG. 25 showing the primary archwire with a clamping bend formed so as to overlap the secondary archwire.
Figure 30:
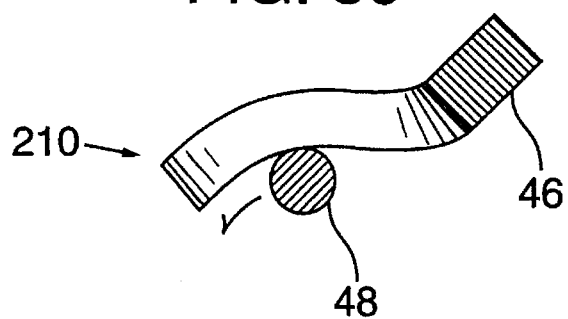
FIG. 30 is a view similar to FIG. 28 showing the bend in the primary archwire clamping the secondary archwire in place in the manner shown in FIG. 28.

FIGS. 29 and 30 show an alternate way to interconnect the archwires, using the archwires themselves. Alongside the bracket 150, a U-shaped bend 210 is formed in archwire 46, in a direction extending over the path of archwire 48. As shown in FIG. 30, this bend can be contoured so as to clamp downward on archwire 48. As a further variation, a complementary U-shaped bend 212 can be formed in the auxiliary archwire so as to extend beneath the path of archwire 46.

Figure 33:
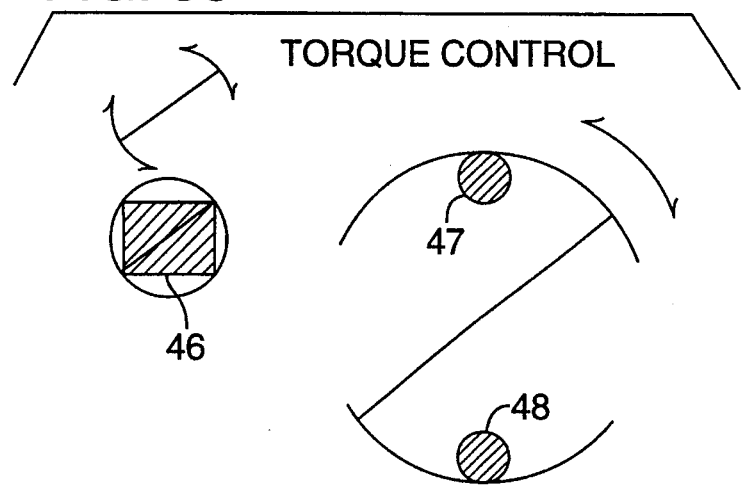
FIGS. 33–35 are cross-sectional views comparing various functional aspects of using a conventional single-arch edgewise bracket and using the multi-arch brackets of FIGS. 11 and 19.
Figure 34:
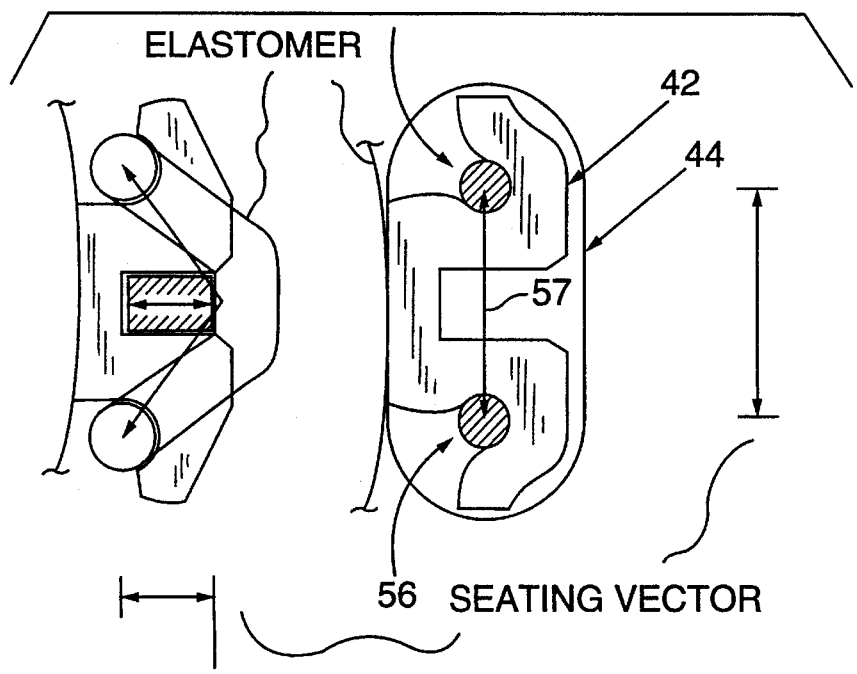
Figure 35:
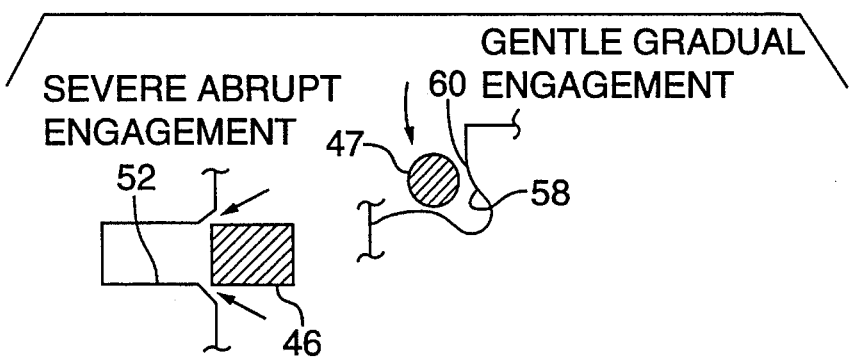

FIGS. 33–35 are cross-sectional views comparing various functional aspects of using a conventional single-arch edgewise bracket and using the multi-arch brackets of FIGS. 11 and 19. The Figures show how the present invention improves over Andrews in several respects.

In FIG. 34, the left side shows the conventional edgewise bracket, with a single rectangular archwire secured in the archwire slots by a conventional elastomer O-ring. The O-ring provides a seating force proportional to its extension transversely of its length as stretched between the tie wings over the archwire. In contrast, the right side of FIG. 34 shows the combination of bracket 42 and resilient interarch connector 44 (or bracket 100 and connector 116 in FIG. 21) securing two archwires 47, 48 in the auxiliary archwire slots 56 under the wings 54 along substantially the same axis 57 as the central archwire slot. In this case, the direction of the seating vector is more nearly parallel to the direction of lengthwise elongation of the interarch connector along the occluso-gingival axis 57, so that the seating forces can be greater than in the prior art. Additionally, less elongation of the interarch connector is needed to place the multiple-wire and interconnect assembly on the brackets, because of both the more direct elongation of the interarch connector and the fact that the wires themselves provide some added resilience. Therefore, the interarch connector need not be as stretchable as conventional elastomer O-rings. This means that the interarch connector can be made of a stiffer (higher Durometer) material than the O-rings, such as polysulfone. This yields the further advantage that such material is tougher and more resistant to mouth fluids, and can be left in place longer, helping to reduce the number of orthodontic treatments required in a course of treatment.

In the left side of FIG. 33, the relative torque control provided in the prior art is essentially that provided by the diagonal dimensions of the rectangular archwire. The right side of FIG. 33 shows that torque control is substantially increased by the present invention, being enhanced by the increased spacing of the auxiliary archwires.

In a treatment situation wherein the archwire cannot initially be fully seated, the ability to partially seat the archwire and have the elastomer gradually pull the archwire into the slot is important. The increased seating force provided as shown in the right side of FIG. 34 is an important factor in being able to accomplish gradual seating. So too is the conformation of the archwire slot, which is shown in FIG. 35. In the conventional archwire and slot shown in the left side of FIG. 35, there can be a binding interengagement of the archwire and slot that obstructs seating. In the auxiliary archwires and slots of the present invention, however, the shape of the archwire and the entry to the archwire slot are configured to facilitate gradual seating. In the illustrated example, the archwire 47 is circular in cross-section and the slot 56, although having a parallel-sided base portion 58, has a funnel-shaped entry or lead-in portion 60, which can be rounded to further facilitate seating.

Having described and illustrated the principles of the invention in a preferred embodiment thereof, it should be apparent that the invention can be modified in arrangement and detail without departing from such principles. For example, the bases of the brackets can be angled or of varying thicknesses. I claim all modifications and variation coming within the spirit and scope of the following claims.

I claim:

1. An improved multiwire orthodontic bracket comprising:

a bracket body having a base for mounting the bracket on a surface of a tooth;

a pair of wings extending in opposite directions from the bracket body;

first and second reentrant archwire slots spaced occluso-gingivally along opposite sides of the bracket beneath the wings;

the slots being sized and shaped to receive and securely hold a cross-sectional dimension of an archwire in a base portion of the slot;

the slots being oriented so that a pair of occluso-gingivally spaced archwires can be inserted into the slots at a nonparallel angle to one another;

the slots each having a base portion with parallel sidewall portions spaced to securely hold the cross-sectional dimension of the archwire and an entry portion that opens generally toward the base of the bracket and is funnel-shaped to guide the archwires gradually into the base portions of the slots to be seated therein.

2. A bracket according to claim 1 in which the angle between the slots is about 90°.

3. A bracket according to claim 1 in which the body of the bracket has an occluso-gingival axis extending between the slots and the angle of the slots relative to said axis is about 45°.

4. A bracket according to claim 1 in which the bracket body includes a third slot formed between the wings with an opening in the face of the body opposite the base of the bracket.

5. A bracket according to claim 4 in which the third slot is rectangular.

6. An improved multiwire orthodontic bracket comprising:

a bracket body having abase for mounting the bracket on a surface of a tooth;

a pair of wings extending in opposite directions from the bracket body;

first and second reentrant archwire slots spaced occluso-gingivally along opposite sides of the bracket beneath the wings;

the slots being sized and shaped to receive and securely hold a cross-sectional dimension of an of an archwire in a base portion of the slot;

the slots being oriented so that a pair off occluso-gingivally spaced archwires can be inserted into the slots at a nonparallel angle to one another;

the bracket body including a third slot formed between the wings with an opening in a face of the body opposite the base of the bracket, the first and second slots each having an entry portion that opens generally toward the base of the bracket and a base portion oriented at an angle to the third slot of about 135°.

7. A bracket according to claim 6 in which the slots each have a base portion with parallel sidewall portions spaced to securely hold the cross-sectional dimension of the archwire and an entry portion that opens generally toward the base of the bracket and is funnel-shaped to guide the archwires gradually into the base portions of the slots to be seated therein.

8. A bracket according to claim 6 in which the first and second slots each have a base portion with parallel sidewall portions spaced to securely hold the cross-sectional dimension of an archwire.

9. A bracket according to claim 6 in which the third slot includes parallel sidewall portions spaced to securely hold the cross-sectional dimension of a rectangular archwire.

10. An interarch connector for spanning three occluso-gingivally spaced archwires, the connector comprising:

a connector body formed of a resilient material suitable for use in the human mouth in orthodontic applications;

the connector body having an axis of elongation;

means defining first and second archwire openings spaced apart along the axis of elongation and sized for first and second occluso-gingivally spaced archwires to be threaded through the openings; and means defining a third archwire openings spaced between the first and second archwire openings for a third archwire to be threaded through the third opening;

the connector body being resiliently deformable predominantly along the axis of elongation to enable the first and second archwires to be spread apart from the third archwire and then to contract the archwires toward one another.

11. An interarch connector according to claim 10 which the connector body is formed of a resilient metal wire spring material wound to form spiral sections defining the first, second and third archwire openings.

12. An interarch connector for spanning two occluso-gingivally spaced archwires, the connector comprising;

a connector body formed of a resilient material suitable for use in the human mouth in orthodontic applications;

the connector body having an axis of elongation;

means defining first and second archwire openings spaced apart along the axis of elongation and sized for first and second occluso-gingivally spaced archwires to be threaded through the openings;

the connector body being resiliently deformable along the axis of elongation to enable the archwires to be spread apart and then to contract the archwires toward one another:

the connector body being formed of a resilient elastomeric material molded to a generally rounded oblong shape with parallel spaced tubular holes defining the first and second archwire openings.

13. An interarch connector according to claim 12 in which the connector body is formed with means defining a third archwire opening spaced between the first and second archwire openings for a third archwire to be threaded through the third opening.

14. An interarch connector for spanning two occluso-gingivally spaced archwires, the connector comprising:

connector body formed of a resilient material suitable for use in the human mouth in orthodontic application;

the connector body having an axis of elongation;

means defining first and archwire openings spaced apart along the axis of elongation and sized for first and second occluso-gingivally spaced archwires to be threaded through the openings;

the connector body being resiliently deformable along the axis of elongation to enable the archwires to be spaced apart and then to contract the archwires toward one another;

the connector body being formed of a resilient metal flat spring material folded to form spiral sections defining the first and second archwire openings.

15. An interarch connector according to claim 14 in which the connector body is formed with means defining a third archwire opening spaced between the first and second archwire openings for a third archwire to be threaded through the third opening.

16. An interarch connector for spanning two occluso-gingivally spaced archwires, the connector comprising:

a connector body including a member formed of a resilient material suitable for use in the human mouth in orthodontic applications;

the connector body having an axis of elongation;

means defining first and second archwire openings spaced apart along the axis of elongation and sized for first and second occluso-gingivally spaced archwires to be threaded through the openings;

the connector body being movable along the axis of elongation to enable the archwires to be spread apart and then to contract the archwires toward one another;

the connector body comprising complementary first and second generally U-shaped members defining a two-part interengaging sliding structure arranged to retain two arch wires in a slot having a variable length, and said member formed of resilient material for securing the two members together in the slot of variable length as the two members are urged toward one another.

17. An interarch spacer for spanning the two occluso-gingivally spaced archwires, the spacer comprising:

a spacer body formed of a rigid material suitable for use in the human mouth in orthodontic applications;

the spacer body being elongated transversely along an occluso-gingival axis;

means defining first and second archwire spacing slots opening in opposite directions along opposite occluso-gingival sides of the spacer body for receiving first and second archwires at a variable depth within the slots;

the slots being spaced a predetermined fixed distance apart along the occluso-gingival axis to maintain the archwires apart at a spacing not less than a minimum occluso-gingival spacing from one another.

18. An interarch spacer according to claim 17 in which the spacer body is formed of a polymeric material molded to a generally rounded oblong shape with parallel spaced channels defining the first and second archwire spacing slots.

19. An interarch connector according to claim 17 in which the spacer body is formed of a metal material extruded to form a generally rounded oblong shape with parallel spaced channels defining the first and second archwire spacing slots.

20. An interarch connector according to claim 17 in which the spacer body is formed of a flat metal material folded to form a generally rounded oblong shape with parallel spaced channels defining the first and second archwire spacing slots.

21. An interarch connector according to claim 17 in which the spacer body is formed with means defining a third archwire opening spaced between the first and second archwire spacing slots for a third archwire to be threaded through the third opening.

22. An interarch spacer according to claim 17 in which the slots are formed with a bend for shaping a segment of the archwires received therein.

23. A multiarch assembly comprising:

first and second parallel archwires, each formed into a segment of an orthodontic archform spanning a plurality of a patient's teeth;

a multiarch bracket having a bracket body including a base for attaching the bracket to a surface of a tooth of the patient and means defining reentrant archwire slots along opposite occluso-gingival sides of the base for receiving and seating the first and second archwires in a base portion therein, the base portions of the slots having a predetermined center-to-center occluso-gingival spacing; and an interarch connector having a connector body formed of a resilient material with first and second archwire openings spaced apart along an occluso-gingival axis of elongation and sized for the first and second archwires to be threaded therethrough, the connector body being resiliently deformable along the axis of elongation to enable the archwires to be spread apart and then to urge the archwires toward one another in a direction of contraction along said axis;

the openings in the interarch connector being spaced center-to-center a distance approximately equal to or less than the center-to-center occluso-gingival spacing between the base portions of the archwire slots on opposite sides of the bracket;

the sidewalls of the archwire slots are shaped to converge toward a parallel relationship to gradually move the archwires into tightly controlled positions seated in the base portion of each slot as the archwires migrate toward the base portions of the slots under the force of contraction of the interarch connector;

whereby the archwires, multiarch bracket and interarch connector exert force on the bracket, and thereby on the patient's teeth, with gradually increasing precision as the occluso-gingivally spaced archwires are urged by contraction of the interarch connector toward one another into the base portions of the spaced slots.

24. A multiarch assembly according to claim 23 in which the reentrant archwire slots in the bracket are oriented at a nonparallel angle to one another so that the archwires received therein are urged deeper into the slots with a force component oriented in a direction transverse to the direction of contraction of the interarch connector.

25. A multiarch assembly according to claim 23 in which the archwire slots have an entrance portion that is wider than a cross-sectional dimension of the archwire to permit the archwires to be partially engaged in the archwire slots notwithstanding differences in position between the bracket and the archwires.

26. A multiarch assembly according to claim 23 including a third archwire, the bracket body including a pair of oppositely-directed wings and a third slot formed between the wings with an opening in a face of the body opposite the base of the bracket to receive the third archwire, and the connector body including a third archwire opening spaced between the first and second archwire openings for the third archwire to be threaded through the third opening.

27. A multiarch assembly according to claim 26 in which the third slot is a three-sided rectangular slot and the third archwire has a rectangular cross section configured to fit within the third slot.

28. A multiarch assembly according to claim 23 in which the bracket body includes a pair of oppositely-directed wings forming the means defining said reentrant archwire slots.

29. A multiarch assembly comprising:

first and second parallel archwires, each formed into a segment of an orthodontic archform spanning a plurality of a patient's teeth;

a multiarch bracket having a bracket body including a base for attaching the bracket to a surface of a tooth of the patient and means defining reentrant archwire slots along opposite occluso-gingival sides of the base for receiving and seating the first and second archwires in a base portion therein, the base portions of the slots having a predetermined center-to-center occluso-gingival spacing; and an interarch connector having a connector body formed of a resilient material with first and second archwire openings spaced apart along an occluso-gingival axis of elongation and sized for the first and second archwires to be threaded therethrough, the connector body being resiliently deformable along the axis of elongation to enable the archwires to be spread apart and then to urge the archwires toward one another in a direction of contraction along said axis;

the openings in the interarch connector being spaced center-to-center a distance approximately equal to or less than the center-to-center occluso-gingival spacing between the base portions of the archwire slots on opposite sides of the bracket;

an interarch spacer defining first and second archwire spacing slots opening in opposite directions along opposite occluso-gingival sides of the spacer body for receiving first and second archwires at a variable depth within the slots, the slots being spaced a predetermined fixed distance apart along the occluso-gingival axis to maintain the archwires at a spacing not less than a minimum occluso-gingival spacing from one another;

whereby the archwires, multiarch bracket, interarch spacer and interarch connector exert force on the bracket, and thereby on the patient's teeth, with gradually increasing precision as the occluso-gingivally spaced archwires are urged by contraction of the interarch connector toward one another into the base portions of the spaced slots.

30. A multiarch assembly according to claim 29 in which the sidewalls of the archwire slots are shaped to converge toward a parallel relationship to gradually move the archwires into tightly controlled positions seated in the base portion of each slot as the archwires migrate toward the base portions of the slots under the force of contraction of the interarch connector.

31. A multiarch assembly according to claim 29 including a third archwire, the bracket body including a pair of oppositely-directed wings and a third slot formed between the wings with an opening in a face of the body opposite the base of the bracket to receive the third archwire, and the connector body including a third archwire opening spaced between the first and second archwire openings for the third archwire to be threaded through the third opening.

32. A multiarch assembly according to claim 31 in which the third slot is a three-sided rectangular slot and the third archwire has a rectangular cross section configured to fit within the third slot.

33. A multiarch assembly comprising:

first, second and third parallel archwires, each formed into a segment of an orthodontic archform spanning a plurality of a patient's teeth;

a multiarch bracket having a bracket body including a base for attaching the bracket to a surface of a tooth of the patient and means defining reentrant archwire slots along opposite occluso-gingival sides of the base for receiving and seating the first and second archwires in a base portion therein, the base portions of the slots having a predetermined center-to-center occluso-gingival spacing;

the bracket body including a pair of oppositely-directed wings and a third slot formed between the wings with an opening in a face of the body opposite, the base of the bracket to receive a third archwire; and an interarch connector having a connector body formed of a resilient material with first and second archwire openings spaced apart along an occluso-gingival axis of elongation and sized for the first and second archwires to be threaded therethrough, the connector body being resiliently deformable along the axis of elongation to enable the archwires to be spread apart and then to urge the archwires toward one another in a direction of contraction along said axis;

the first and second archwire openings in the interarch connector being spaced center-to-center a distance approximately equal to or less than the center-to-center occluso-gingival spacing between the base portions of the archwire slots on opposite sides of the bracket; and the connector body including a third archwire opening spaced between the first and second openings for the third archwire to be threaded through the third opening;

whereby the archwires, multiarch bracket and interarch connector exert force on the bracket, and thereby on the patient's teeth, with gradually increasing precision as the occluso-gingivally spaced archwires are urged by contraction of the interarch connector toward one another into the base portions of the spaced slots.

* * * * *